US012779010B1

(12) United States Patent
Garber, II et al.

(10) Patent No.: US 12,779,010 B1
(45) Date of Patent: Nov. 3, 2026

(54) VASOPRESSIN PREMIX SYSTEMS AND USES THEREOF

(71) Applicants: Baxter International Inc., Deerfield, IL (US); Baxter Healthcare SA, Glattpark (CH)

(72) Inventors: Robert W. Garber, II, Island Lake, IL (US); Sydney Cope, Chicago, IL (US); Jason Mantei, Volo, IL (US); Mark Doty, Brookings, SD (US)

(73) Assignees: Baxter International Inc., Deerfield, IL (US); Baxter Heathcare, SA, Glattpark (CH)

( * ) Notice: Subject to any disclaimer, the term of this patent is extended or adjusted under 35 U.S.C. 154(b) by 0 days.

(21) Appl. No.: 19/362,006

(22) Filed: Oct. 17, 2025

Related U.S. Application Data

(60) Division of application No. 18/907,424, filed on Oct. 4, 2024, now Pat. No. 12,447,190, which is a continuation of application No. 18/900,547, filed on Sep. 27, 2024.

(60) Provisional application No. 63/587,055, filed on Sep. 29, 2023.

(51) Int. Cl.

| | |
|---|---|
| ***A61K 38/095*** | (2019.01) |
| ***A61J 1/14*** | (2023.01) |
| ***A61K 9/00*** | (2006.01) |
| ***A61K 47/02*** | (2006.01) |
| ***A61K 47/12*** | (2006.01) |

(52) U.S. Cl.
CPC ........... *A61K 38/095* (2019.01); *A61J 1/1468* (2015.05); *A61K 9/0019* (2013.01); *A61K 47/02* (2013.01); *A61K 47/12* (2013.01)

(58) Field of Classification Search
CPC .... A61K 38/095; A61K 9/0019; A61J 1/1468
See application file for complete search history.

(56) References Cited

U.S. PATENT DOCUMENTS

| | | | |
|---|---|---|---|
| 3,835,110 | A | 9/1974 | Greven |
| 9,750,785 | B2 | 9/2017 | Kenney et al. |
| 9,919,026 | B2 | 3/2018 | Kenney et al. |
| 10,844,435 | B1 | 11/2020 | Vijayan |
| 10,920,278 | B1 | 2/2021 | Vijayan |
| 11,684,573 | B1 | 6/2023 | Ma et al. |
| 2022/0133838 | A1 | 5/2022 | Kenney et al. |
| 2023/0190639 | A1 | 6/2023 | Kocherlakota et al. |
| 2023/0256048 | A1 | 8/2023 | Kenney et al. |
| 2023/0303305 | A1 | 9/2023 | Abrams et al. |

FOREIGN PATENT DOCUMENTS

| | | |
|---|---|---|
| EP | 2326341 B1 | 4/2012 |
| LT | 4487 B | 4/1999 |

OTHER PUBLICATIONS

Vasostrict (Vasopressin in 5% Dextrose Injection) Ready to Use 50mL × 10 Single Dose Vials [product label]; Par Pharmaceutical; 2014.

Van Matre et al., Hospital Pharmacy Apr. 1, 2023, 58(2) 205-211.

*Primary Examiner* — Gyan Chandra
(74) *Attorney, Agent, or Firm* — Womble Bond Dickinson (US) LLP

(57) ABSTRACT

Provided is a system comprising a flexible container for intravenous administration which comprises a premix vasopressin pharmaceutical formulation, and uses thereof.

28 Claims, 7 Drawing Sheets

FIG. 1

| Impurity | IUPAC Chemical Name | Chemical Structure | Process/ Degradation Impurity | Source/ Mechanism | Proposed Acceptance Criteria | Justification |
|---|---|---|---|---|---|---|
| Related Compound N | N1 | H-Cys-Tyr-Phe-Gln-Asn-Cys-Pro-Arg-Gly-OH | Degradation Impurities | Deomidation of amino acid residues (glycine) | 1.0% | Acceptance Criteria = Qualification Threshold |
| | N2 | H-Cys-Tyr-Phe-Glu-Asn-Cys-Pro-Arg-Gly-NH2 | | Deamidation of amino acid residues (glutamine and asparagine) | | |
| | | H-Cys-Tyr-Phe-Glu-Asp-Cys-Pro-Arg-Gly-NH2 | | | | |

FIG. 5

| Test | | Acceptance Criteria | Test Results from Certificate of Analysis | | |
|---|---|---|---|---|---|
| | | | 561372-1 | 561372-2 | 561372-3 |
| pH at 25°C | | 3.6 - 4.0 | 3.9 | 3.9 | 3.9 |
| Identification by Retention Time Match | | Positive: The retention time of the vasopressin peak in the sample solution is within ± 5% of the mean retention time of vasopressin in bracketing standard injections | Positive | Positive | Positive |
| Identification by Spectral Match | | Positive: The wavelength maximum and minimum of the vasopressin peak in the sample solution are within ± 2nm of the mean peak maximum and minimum respectively in bracketing standard injections. The absorbance ratio in the sample is within ± 5% of the mean absorbance ratio of the standards | Positive | Positive | Positive |
| Vasopressin Assay | | 0.180-0.220 U/mL (90.0% - 110.0% Label Claim) | 0.201 U/mL (100.7%) | 0.200 U/mL (100.1%) | 0.201 U/mL (100.3%) |
| Related Compounds | Related Compound N | NMT 1.0% | NMT 0.50% | NMT 0.50% | NMT 0.50% |
| | Any Other Individual Related Compound | NMT 1.0% | NMT 0.50% | NMT 0.50% | NMT 0.50% |
| | Total Related Compounds | NMT 2.0% | NMT 0.50% | NMT 0.50% | NMT 0.50% |
| Osmolality | | 255-345 mOsm/kg | 288 mOsm/kg | 292 mOsm/kg | 292 mOsm/kg |
| Visual Appearance | | Pass. Pass means a clear, colorless solution by visual inspection | Pass | Pass | Pass |

FIG. 5 con.

| Test | Acceptance Criteria | Test Results from Certificate of Analysis | | |
|---|---|---|---|---|
| | | 561372-1 | 561372-2 | 561372-3 |
| Particulate Matter | Particles ≥ 10 µm: NMT 60 counts/mL<br>Particles ≥ 25 µm: NMT 6 counts/mL | 0 counts/mL<br>0 counts/mL | 0 counts/mL<br>0 counts/mL | 0 counts/mL<br>0 counts/mL |
| Bacterial Endotoxins | 20 Units/100 mL: NMT 3.4 EU/mL | < 0.0500 EU/mL | < 0.0500 EU/mL | < 0.0500 EU/mL |
| Sterility | Sterile (Pass) | Pass | Pass | Pass |
| Fill Volume[a] | 103.5 – 106.5 mL (Pass) | Pass | Pass | Pass |
| Air Volume[a] | 10.0 – 25.0 cc (Pass) | Pass | Pass | Pass |

[a] In-process controls fill volume and air volume are an alternate test to extractable volume as indicated in 3.2.P.5.1 Specification(s). Pass indicates that no exceptions were observed during the filling process.

| Test | | Acceptance Criteria | Test Results from Certificate of Analysis | | |
|---|---|---|---|---|---|
| | | | 561834-1 | 561834-2 | 561834-4 |
| pH at 25°C | | 3.6 - 4.0 | 3.9 | 3.9 | 3.9 |
| Identification by Retention Time Match | | Positive: The retention time of the vasopressin peak in the sample solution is within ± 5% of the mean retention time of vasopressin in bracketing standard injections. | Positive | Positive | Positive |
| Identification by Spectral Match | | Positive: The wavelength maximum and minimum of the vasopressin peak in the sample solution are within ± 2nm of the mean peak maximum and minimum respectively in bracketing standard injections. The absorbance ratio in the sample is within ± 5% of the mean absorbance ratio of the standards. | Positive | Positive | Positive |
| Vasopressin Assay | | 0.360-0.440 U/mL (90.0% - 110.0% Label Claim) | 0.405 U/mL (101.2%) | 0.400 U/mL (100.1%) | 0.413 U/mL (103.2%) |
| Related Compounds | Related Compound N | NMT 1.0% | NMT 0.50% | NMT 0.50% | NMT 0.50% |
| | Any Other Individual Related Compound | NMT 1.0% | NMT 0.50% | NMT 0.50% | NMT 0.50% |
| | Total Related Compounds | NMT 2.0% | NMT 0.50% | NMT 0.50% | NMT 0.50% |
| Osmolality | | 255-345 mOsm/kg | 290 mOsm/kg | 290 mOsm/kg | 299 mOsm/kg |
| Visual Appearance | | Pass. Pass means a clear, colorless solution by visual inspection. | Pass | Pass | Pass |
| Particulate Matter | | Particles ≥ 10 µm: NMT 60 counts/mL<br>Particles ≥ 25 µm: NMT 6 counts/mL | 0 counts/mL<br>0 counts/mL | 0 counts/mL<br>0 counts/mL | 0 counts/mL<br>0 counts/mL |
| Bacterial Endotoxins | | 40 Units/100 mL. NMT 6.8 EU/mL | < 0.0200 EU/mL | < 0.0200 EU/mL | < 0.200 EU/mL |
| Sterility | | Sterile (Pass) | Pass | Pass | Pass |
| Fill Volumes | | 103.5 – 106.5 mL (Pass) | Pass | Pass | Pass |
| Air Volumes | | 10.0 – 25.0 cc (Pass) | Pass | Pass | Pass |

FIG. 6

VASOPRESSIN PREMIX SYSTEMS AND USES THEREOF

RELATED APPLICATIONS

This application is a divisional of U.S. Non-Provisional application Ser. No. 18/907,424 filed Oct. 4, 2024, now issued as U.S. Pat. No. 12,447,190, which is a continuation of U.S. Non-Provisional application Ser. No. 18/900,547, filed Sep. 27, 2024, which claims priority to U.S. Provisional Application No. 63/587,055, filed on Sep. 29, 2023. The contents of the foregoing are incorporated by reference herein.

BACKGROUND

Vasopressin (also called arginine-vasopressin, AVP, or antidiuretic hormone ADH) is a peptide hormone that regulates the tonicity of bodily fluids and has vasoconstrictive effects when administered. In particular vasopressin can be used to increase blood pressure in patients who are in vasodilatory shock, for example in patients who have acute circulatory failure and/or are in shock.

For intravenous injection, vasopressin is often provided in a concentrated formulation, and diluted into an intravenous (IV) bag prior to delivery. Such delivery can be prone to error, where dilution is necessary under circumstances which can be challenging given the nature of the patient's condition. Improvements in vasopressin delivery are needed in the art.

SUMMARY

The disclosure herein provides compositions and uses thereof that improve delivery of vasopressin to a human patient. More specifically, provided herein is a stable vasopressin formulation which is contained within a primary container which is an intravenous (IV) bag, which is ready to use and does not require dilution of the formulation prior to administration to a human patient in need thereof. Collectively this system, including, a sealed IV bag containing a stable pharmaceutical formulation comprising vasopressin which is ready to use and does not require dilution, provides an efficient and safe means of delivering vasopressin to patients, who may need the drug on an urgent basis.

One aspect provides a sealed container system for stable storage of a premix vasopressin formulation, the sealed container system comprising a primary container comprising a premix vasopressin formulation, wherein the premix vasopressin formulation is an aqueous formulation, has a pH of about 3.1 and to 4.5, and comprises about 0.1 unit/mL to about 1.0 unit/mL vasopressin or about 180 ng/ml to about 910 ng/mL vasopressin, an osmolality agent, and a buffer, wherein the primary container is a multi-layer plastic container comprising a layer of polyethylene, wherein the primary container is a bag having a volume of 50 mL to 500 mL.

In one embodiment, the osmolality agent is sodium chloride. In certain embodiments, the concentration of sodium chloride is about 8.5 mg/mL to about 9.5 mg/mL. In other embodiments, the concentration of sodium chloride is about 9 mg/mL.

In one embodiment, the osmolality agent is dextrose, e.g., a pharmaceutical premix vasopressin formulation comprising 5% dextrose.

In some embodiments, the pharmaceutical premix formulation has a concentration of vasopressin of about 0.2 unit/mL to about 1 unit/mL vasopressin; about 0.1 unit/mL to about 0.5 unit/mL vasopressin; about 0.2 unit/mL to about 0.4 unit/mL vasopressin; or about 360 ng/mL to about 730 ng/mL vasopressin. In other embodiments, the concentration of vasopressin is about 0.2 unit/mL, about 0.4 unit/mL, about 360 ng/ml, or about 730 ng/mL.

In some embodiments, the premix vasopressin formulation has a pH between about 3.6 and about 4.0.

In some embodiments, the buffer is a lactate salt. In certain embodiments, the concentration of the lactate salt is about 2.5 mM to about 3.5 mM. In other embodiments, the lactate salt is about 280 μg/mL to about 400 μg/mL. In another embodiment, the concentration of the lactate salt is about 3 mM. In yet another embodiment, the concentration of the lactate salt is about 336 μg/mL.

Also provided herein is a sealed container system for stable storage of a premix vasopressin formulation, the sealed container system comprising a primary container comprising a premix vasopressin formulation comprising about 0.1 unit/mL to about 1 unit/mL vasopressin, about 8.5 mg/mL to about 9.5 mg/mL sodium chloride, about 2.5 mM to about 3.5 mM or about 280 μg/mL to about 400 μg/mL of a lactate salt, wherein the premix vasopressin formulation is an aqueous formulation and has a pH of about 3.1 to about 4.5, and wherein the primary container is a multi-layer plastic container comprising a layer of polyethylene, wherein the primary container is a bag having a volume of 50 mL to 500 mL. In certain embodiments, the premix vasopressin formulation also comprises a pH adjustor(s) which is sodium hydroxide and/or hydrochloric acid.

Also provided herein is a sealed container system for stable storage of a premix vasopressin formulation, the sealed container system comprising a primary container comprising a premix vasopressin formulation comprising about 0.1 unit/mL to about 1 unit/mL vasopressin, about 8.5 mg/mL to about 9.5 mg/mL sodium chloride, about 2.5 mM to about 3.5 mM of a lactate salt, wherein the premix vasopressin formulation is an aqueous formulation and has a pH of about 3.1 to about 4.5, and wherein the primary container is a multi-layer plastic container comprising a layer of polyethylene, wherein the primary container is a bag having a volume of 50 mL to 500 mL. In certain embodiments, the premix vasopressin formulation also comprises a pH adjustor(s) which is sodium hydroxide and/or hydrochloric acid.

Also provided herein is a sealed container system for stable storage of a premix vasopressin formulation, the sealed container system comprising a primary container comprising a premix vasopressin formulation comprising about 180 ng/ml to about 910 ng/mL vasopressin, about 8.5 mg/mL to about 9.5 mg/mL sodium chloride, about 280 μg/mL to about 400 μg/mL of a lactate salt, wherein the premix vasopressin formulation is an aqueous formulation and has a pH of about 3.1 to about 4.5, and wherein the primary container is a multi-layer plastic container comprising a layer of polyethylene, wherein the primary container is a bag having a volume of 50 mL to 500 mL. In certain embodiments, the premix vasopressin formulation also comprises a pH adjustor(s) which is sodium hydroxide and/or hydrochloric acid.

Yet another aspect described herein is a sealed container system for stable storage of a premix vasopressin formulation, the sealed container system comprising a primary container comprising a premix vasopressin formulation consisting essentially of about 0.1 unit/mL to about 1 unit/mL vasopressin; about 9 mg/mL sodium chloride, about 3 mM of a lactate salt, wherein the premix vasopressin formulation is an aqueous formulation and has a pH of about 3.5 to about 4.1, and wherein the primary container is a multi-layer plastic container comprising a layer of polyethylene, wherein the primary container is a bag having a volume of 50 mL to 500 mL. In certain embodiments, the premix vasopressin formulation also comprises a pH adjustor(s) which is sodium hydroxide and/or hydrochloric acid.

Another aspect described herein is a sealed container system for stable storage of a premix vasopressin formulation, the sealed container system comprising a primary container comprising a premix vasopressin formulation consisting essentially of about 0.1 unit/mL to about 1 unit/mL vasopressin; about 9 mg/mL sodium chloride, about 336 μg/mL a lactate salt, wherein the premix vasopressin formulation is an aqueous formulation and has a pH of about 3.5 to about 4.1, and wherein the primary container is a multi-layer plastic container comprising a layer of polyethylene, wherein the primary container is a bag having a volume of 50 mL to 500 mL. In certain embodiments, the premix vasopressin formulation also comprises a pH adjustor(s) which is sodium hydroxide and/or hydrochloric acid.

In one embodiment, the premix vasopressin formulation comprises about 0.2 unit/mL to about 1 unit/mL vasopressin.

In another embodiment, the premix vasopressin formulation comprises about 0.1 unit/mL to about 0.5 unit/mL vasopressin.

In still another embodiment, the premix vasopressin formulation comprises about 0.2 unit/mL to about 0.4 unit/mL vasopressin.

In a further embodiment, the premix vasopressin formulation comprises about 360 ng/ml to about 730 ng/mL vasopressin.

In certain embodiments, the premix vasopressin formulation comprises about 0.1 unit/mL.

In other embodiments, the premix vasopressin formulation comprises about 0.4 unit/mL.

In yet other embodiments, the premix vasopressin formulation comprises about 360 ng/mL.

In certain other embodiments, the premix vasopressin formulation comprises about 730 ng/ml vasopressin.

In one embodiment, the lactate salt is sodium lactate. In one embodiment, the lactate salt is sodium DL lactate.

In certain embodiments, the premix vasopressin formulation further comprises sodium hydroxide and/or hydrochloric acid as pH adjusters.

In one embodiment, the primary container is an intravenous (IV) bag. In one embodiment, the primary container has a volume of 50 mL to 250 mL. For example, the primary container may contain a volume of about 100 mL and contains the premix vasopressin formulation of about 100 mL.

In one embodiment, the primary container is an IV bag having a volume if 100 mL and comprising 20 units/100 mL vasopressin (0.2 units/mL) or 40 units/100 mL vasopressin (0.4 units/mL) in 0.9% sodium chloride and comprising sodium lactate.

The premix vasopressin formulation described herein is suitable for intravenous administration to a human subject.

In one embodiment, the primary container containing the formulation has a single port, the single port comprising an administration port for delivering the premix vasopressin formulation to a subject.

Described herein is also a method of increasing blood pressure in a human subject, the method comprising intravenously administering a therapeutically effective amount of the premix vasopressin formulation of the sealed container system described herein, to the human subject who is in need of increased blood pressure. In one embodiment, the formulation is administered to the human subject via an infusion tube connected to the sealed container system (IV bag) without diluting the premix vasopressin formulation prior to administration to the human subject.

Provided herein is a method of increasing blood pressure in a human subject in need of increased blood pressure, the method comprising: intravenously administering a therapeutically effective amount of a premix vasopressin formulation in a sealed container system; for stable storage of a pharmaceutical premix vasopressin formulation to the human subject who is in need of increased blood pressure, wherein the sealed container system comprises a primary container, which is an IV bag, comprising a premix vasopressin formulation, wherein the premix vasopressin formulation is an aqueous formulation having a pH of about 3.1 and to 4.5 and comprising about 0.1 unit/mL to about 1.0 unit/mL vasopressin or about 180 ng/mL to about 910 ng/mL vasopressin, sodium chloride, and sodium lactate, wherein the primary container is an intravenous bag having a volume of 50 mL to 500 mL.

In one embodiment, the human subject has vasodilatory shock. In another embodiment, the human subject has vasodilatory shock and remains hypotensive despite fluids and catecholamines.

In certain embodiments, the premix vasopressin formulation is administered to the human subject at a rate of about 0.03 to 0.1 units vasopressin per minute, wherein the subject has post-cardiotomy shock.

In other embodiments, the premix vasopressin formulation is administered to the human subject the premix vasopressin formulation at a rate of about 0.01 to 0.07 units vasopressin per minute, wherein the subject has septic shock.

BRIEF DESCRIPTION OF DRAWINGS

FIG. 1 describes Related Compound N, also referred to as Impurity N.

FIG. 5 depicts batch analysis for three lots of the 0.2 units/mL vasopressin formulation.

FIG. 6 depicts batch analysis for three lots of the 0.4 units/mL vasopressin formulation.

DETAILED DESCRIPTION

Figure 2:
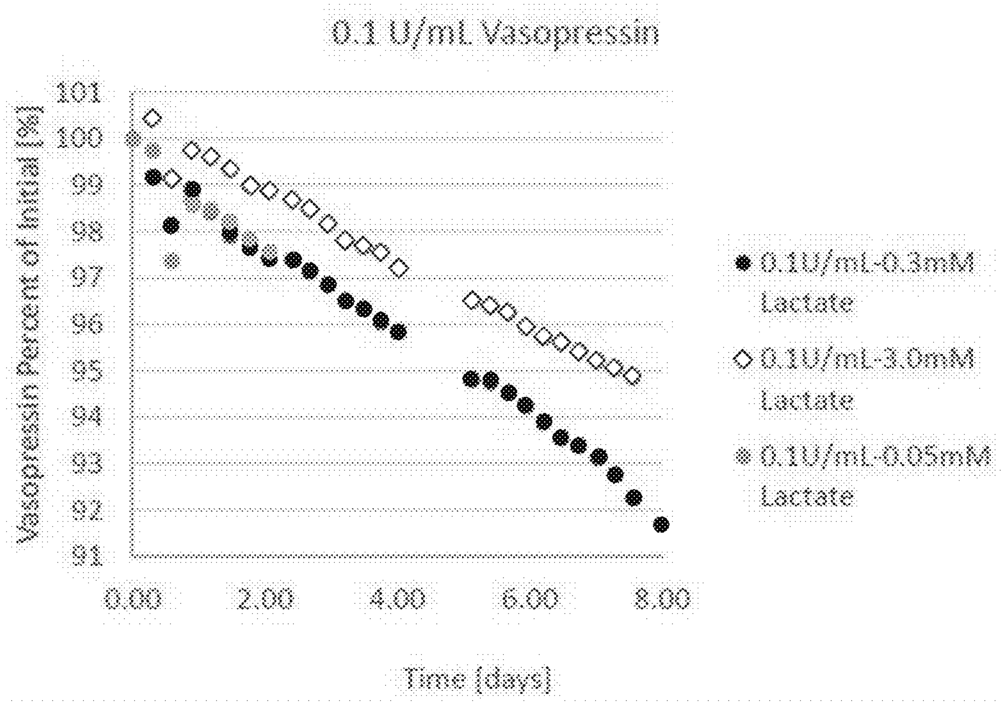
FIG. 2 depicts the amount of vasopressin (% of initial) in the 0.1 U/mL vasopressin premix formulations with varied lactate concentrated as indicated.

The disclosed liquid vasopressin premix pharmaceutical formulation and containers containing said formulation are advantageous in reducing the risk of contamination and errors associated with dilution, providing time savings, convenience, and reducing waste by eliminating the need for such dilution. The vasopressin formulations provided herein are ready to use pharmaceutical premix formulations in order to minimize any medication errors and to make administration of midazolam formulations easier for medical professionals for use in an infusion regimen. Further, the pharmaceutical premix formulations described herein are stable.

Definitions

With respect to the terms used in this disclosure, the following definitions are provided. This application will use the following terms as defined below unless the context of the text in which the term appears requires a different meaning.

As used herein, the term "premix" refers to a ready to use, liquid, aqueous solution suitable for direct administration to human patients, including IV infusion, without requiring dilution prior to administration. "Premix" indicates the formulation is already mixed and is suitable for administration to a human patient. Preferably, the premix solution is supplied as a sterile solution, and is stable over its shelf life, as described herein.

The term "pharmaceutical formulation" refers to a preparation which is in such form as to permit the biological activity of an active ingredient, e.g., vasopressin, contained therein to be effective, and which contains no additional components which are unacceptably toxic to a subject to which the formulation would be administered.

The term "aqueous" when used in reference to a formulation refers to a liquid formulation in which the solvent is water (e.g., water for injection (WFI)).

As used herein, the term "sterile" is understood to mean free from any bacteria or other living microorganisms. For example, a primary container holding the sterile composition does not contain replicating microorganisms and has not been compromised such that it has been exposed to ambient atmosphere and/or biological contaminants. In pharmaceutical practice, a state of sterility exists when the probability is no more than one out of one million that the composition is contaminated with replicating microorganisms. Sterile compositions in accordance with the invention are generally prepared in accordance with current Good Manufacturing Practice ("CGMP") regulations of the U.S. Food and Drug Administration.

A "stable" formulation is one in which the active ingredient therein, e.g. vasopressin, essentially retains its physical and chemical stability, therefore its biological activity, upon storage.

A "patient," "subject" or "individual," used interchangeably herein, is a mammal, preferably a human. A "patient" as used herein refers to a subject or an individual having or suspected of having a disease or a condition, or in need of or undergoing treatment.

As used herein, an "effective amount" is an amount of an active ingredient that provides a nutritional, physiological, or medical benefit to the individual. In one embodiment, an effective amount of vasopressin is an amount that provides for increasing blood pressure.

The term "pharmaceutically acceptable" as used herein refers to substances that do not cause substantial adverse allergic or immunological reactions when administered to a subject.

The terms "substantially no," "essentially free" or "substantially free" as used in reference to a particular component means that any of the component present constitutes less than about 3.0% by weight, such as less than about 2.0% by weight, less than about 1.0% by weight, preferably less than about 0.5% by weight or, more preferably, less than about 0.1% by weight.

The phrase "consists essentially of" or "consisting essentially of" as used interchangeably herein in reference to a pharmaceutical premix formulation, means that the formulation necessarily includes the listed ingredients and is open to unlisted ingredients that do not materially affect the basic nature or stability of the pharmaceutical premix formulation, e.g., liquid, sterile, or the activity of the active ingredient, i.e., vasopressin.

As used herein, the term "about" means +/−10% of any recited value, or in an alternative embodiment, +/−5% of any recited value. As used herein, this term modifies any recited value, range of values, or endpoints of one or more ranges.

As used herein, the term "injectable pharmaceutical formulation" refers to a composition suitable for administration to a human patient or subject that is essentially free of visible particulates, for example, a composition meeting the requirements of United States Pharmacopeia 33, Chapter; Injections.

Vasopressin Pharmaceutical Premix Formulations

A pharmaceutical premix vasopressin formulation disclosed herein provides multiple advantages over the art for intravenous administration. Generally, vasopressin injection is available as a concentrated solution which needs to be diluted to achieve the desired concentration before administration to a human patient as an intravenous bolus or continuous intravenous infusion. Once the diluted vasopressin solution is prepared, it is typically not held for more than 18 hours at room temperature or 24 hours under refrigerated conditions.

Disclosed herein are premix aqueous formulations having an amount of vasopressin that is suitable for administering to a human patient without first diluting the formulation. A pharmaceutical premix formulation described herein has a vasopressin concentration suitable to administer a desired effective dose to a human patient-thus improving efficiency and also minimizing the potential for error that may result from the dilution process. Generally, pharmaceutical premix formulations described herein have a low concentration of vasopressin, e.g., which does not require dilution prior to be administered to a patient for sedation. The premix vasopressin formulations described herein are stable in the flexible IV bag in which they are housed. Together the primary container and the pharmaceutical premix formulation provide a system which is stable for extended period of times and is ready for use without additional preparation, e.g., dilution, steps.

The pharmaceutical premix formulations described herein include vasopressin, which is a polypeptide hormone. Vasopressin causes vasoconstriction by binding to V1 receptors on vascular smooth muscle coupled to the Gq/11-phospholipase C-phosphatidyl-inositol-triphosphate pathway, resulting in the release of intracellular calcium. In addition, vasopressin stimulates antidiuresis via stimulation of V2 receptors which are coupled to adenyl cyclase. The chemical name of vasopressin is Cyclo (1-6) L-Cysteinyl-L-Tyrosyl-L-Phenylalanyl-L-Glutaminyl-L-Asparaginyl-L-Cysteinyl-L-Prolyl-L-Arginyl-L-Glycinamide. The structural formula of vasopressin is described below:

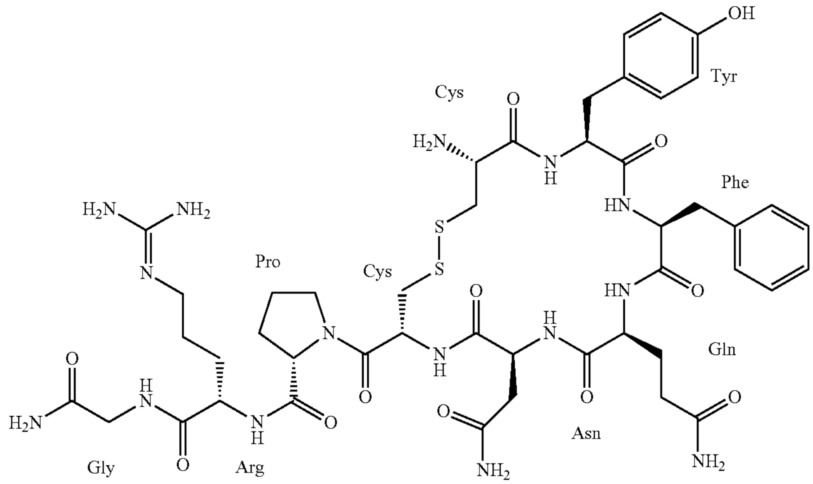 [SMILES: NC(=O)CC[C@@H]1NC(=O)[C@H](Cc2ccccc2)NC(=O)[C@H](Cc2ccc(O)cc2)NC(=O)[C@@H](N)CSSC[C@@H](C(=O)N2CCC[C@H]2C(=O)N[C@@H](CCCN=C(N)N)C(=O)NCC(N)=O)NC(=O)[C@H](CC(N)=O)NC1=O ; "Arg" ; "Gly"]

The peptide sequence Cys-Thr-Phe-Gln-Asn-Cys-Pro-Arg-Gly having the following structure:

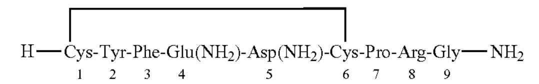

Vasopressin has a molecule formula of $C_{46}H_{65}N_{15}O_{12}S_2$ and a molecular weight of 1084.23. Premix formulations described herein include vasopressin as described above according to either formula.

In one embodiment, the injectable formulation described herein is a sterile aqueous formulation of synthetic arginine vasopressin.

In certain embodiments, a premix vasopressin formulation described herein has no more than 4% Related Compound N (see FIG. 1) when stored at 25° C. for 6 months. In other embodiments, the premix vasopressin formulation comprises no more than 3.9%, no more than 3.8%, no more than 3.7%, no more than 3.6%, no more than 3.5%, no more than 3.4%, no more than 3.3%, no more than 3.2%, no more than 3.1%, no more than 3%, no more than 2.5%, no more than 2%, no more than 1.5%, no more than 1.4%, no more than 1.3%, no more than 1.2%, no more than 1.1%, no more than 1%, no more than 0.9%, or no more than 0.5% Related Compound N. The percentage of Related Compound N can be determined following storage of the formulation for a certain time period at a given temperature, e.g., when stored at 5° C. or 25° C. for 6 months. Without wishing to be bound by theory, Related Compound N is the major impurity generated in a vasopressin formulation when stored for a given time period. In specific embodiments, Related Compound N is the only significant impurity generated in the vasopressin formulation provided herein at 25° C. or 5° C. for a given time period, e.g., 3 months or 6 months. In one embodiment, little to no detectable impurity is found in a vasopressin formulation described herein when stored at 5° C. for a given time period, e.g., 3 months or 6 months.

In one embodiment, a premix vasopressin formulation is an aqueous formulation, has a pH of about 3.1 and to 4.5, and comprises about 0.1 unit/mL to about 1.0 unit/mL vasopressin, an osmolality agent, and a buffer. In one embodiment, a premix vasopressin formulation is an aqueous formulation, has a pH of about 3.1 and to 4.5, and comprises about 180 ng/mL to about 910 ng/mL, an osmolality agent, and a buffer.

In one embodiment, the osmolality agent is sodium chloride. In certain embodiments, the concentration of sodium chloride is about 8.5 mg/mL to about 9.5 mg/mL. In other embodiments, the concentration of sodium chloride is about 9 mg/mL. The ready-to-use vasopressin formulation of the invention can maintain its stability and potency when sodium chloride alone is used as the aqueous tonicity agent.

Amounts, e.g., the amount of sodium chloride, in the pharmaceutical premix formulation may be described in terms of percentage by weight per volume (w/v), e.g., 0.9% sodium chloride, or by concentration in the pharmaceutical premix formulation, e.g., 9.0 mg/mL sodium chloride. Concentrations of components of the formulation may also be expressed in terms of molarity (e.g., M or mM); the number of moles or millimoles per liter, respectively.

In one embodiment, the amount of salt, e.g., sodium chloride, is described in terms of the w/v % of the liquid solution. For example, the pharmaceutical premix formulation may contain from about 0.7% to about 1.1% sodium chloride, about 0.8% to about 1.0% sodium chloride, or about 0.9% sodium chloride.

In one embodiment, the osmolality agent is dextrose. In certain embodiments, the concentration of dextrose is about 3% to about 7%, such as about 3%, 4%, 5%, 6%, or 7%. In other embodiments, the concentration of dextrose is about 4.5%, 5%, or 5.5%.

The osmolality of the pharmaceutical premix formulation comprising vasopressin should be suitable for administration (e.g., intravenous administration) to a subject (e.g., a human patient), e.g., isotonic or near isotonic. For example, the formulation can have an osmolality from about 270 to about 300 mOsm/kg, such as from about 280 to about 290 mOsm/kg, or about 285 mOsm/kg. The formulation can have an osmolarity from about 290 to about 323 mOsm/L, such as from about 300 to about 312 mOsm/L, or about 306 mOsm/L.

One feature of the pharmaceutical premix formulation described herein is the relatively low concentration of vasopressin, such that dilution of the vasopressin pharmaceutical premix formulation is not required. The ready-to-use, stable pharmaceutical premix formulation described herein does not require mixing or diluting prior to delivery to a subject, e.g., a human patient. In certain embodiments, a pharmaceutical premix formulation has about 0.2 unit/mL to about 1 unit/mL vasopressin; about 0.1 unit/mL to about 0.5 unit/mL vasopressin; about 0.2 unit/mL to about 0.4 unit/mL vasopressin; about 0.2 units/mL; or about 0.4 units/mL. "Unit" can be interchangeably referred to as "U."

In certain embodiments, 1 unit of vasopressin corresponds to about 1.815 μg of vasopressin. In certain embodiments, a pharmaceutical premix formulation has a concentration of vasopressin of about 180 ng/ml to about 910 ng/ml; about 360 ng/ml to about 730 ng/ml; about 360 ng/ml; or about 730 ng/mL.

The pH of the pharmaceutical premix formulation described herein is a pH that maintains the stability vasopressin. The pH of the pharmaceutical premix formulation can be in the range of about 2.0 to about 5.0, or a pH of, for example, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0 (ranges including the numbers described herein are also contemplated, e.g., 2.5 to 4.5 or 3.0 to 4.0). In some embodiments, the premix vasopressin formulation has a pH between about 3.6 and about 4.0. In one embodiment, the remix vasopressin formulation has a pH of 3.8.

The pH of the solution may be adjusted by use of a pH adjusting agent, and optionally, if needed a buffer may be used to maintain the pH in the said range. The pH adjusting agent that may be used includes sodium hydroxide, and/or hydrochloric acid.

In some embodiments, the premix vasopressin formulation has a pH between about 3.6 and about 4.0. In other embodiments, the premix vasopressin formulation has a pH of 2.5 to 4.5.

In some embodiments, the buffer included in a vasopressin premix formulation described herein is a lactate salt. As used herein, the terms "sodium lactate" and "lactate salt" each refer to sodium D,L-lactate, unless otherwise specified. As noted below in the examples, both sodium D,L-lactate and sodium D-lactate were found to be essentially equivalent buffers for a vasopressin premix formulation. In certain embodiments, the concentration of the lactate salt or sodium D-lactate is about 2.5 mM to about 3.5 mM. In other embodiments, the premix formulation comprises about 280 μg/mL to about 400 μg/mL lactate salt or sodium D-lactate. In another embodiment, the premix formulation comprises about 3 mM lactate salt or sodium D-lactate. In yet another embodiment, the concentration of the lactate salt or sodium D-lactate is about 336 μg/mL.

In certain embodiments, lactate salt in the formulation is sodium D,L-lactate. In certain embodiments, the concentration of sodium D,L-lactate in the formulation is about 2.5 mM (about 280 μg/mL) to about 3.5 mM (about 392 μg/mL). In another embodiment, the premix formulation comprises about 3 mM (about 336 μg/mL) sodium D,L-lactate.

In certain embodiments, lactate salt in the formulation is sodium D-lactate. In certain embodiments, the concentration of sodium D-lactate in the formulation is about 2.5 mM (about 280 μg/mL) to about 3.5 mM (about 392 μg/mL). In another embodiment, the premix formulation comprises about 3 mM (about 336 μg/mL) sodium D-lactate.

In certain embodiments, a premix vasopressin formulation described herein does not comprise a preservative and/or acetate buffer.

The vasopressin formulation provided herein is stable in that the vasopressin essentially retains its physical and chemical stability, therefore its biological activity, upon storage. The pharmaceutical premix formulation of the disclosure may be characterized according to stability, such as long-term stability to storage. A stable formulation described herein can retain at least about 85%, at least about 86%, at least about 87%, at least about 88%, at least about 89%, 90%, at least about 95%, and/or at least about 99% of vasopressin biological activity upon storage for a given period of time, or over the shelf life of the product, for example for at least 3 months, at least 4 months, at least 5 months, at least 6 months, at least 12 months, at least 15 months, at least 18 months, at least 21 months, or at least 24 months of storage at 5° C.; or after at least 1 month, at least 2 months, at least 3 months, at least 4 months, at least 5 months, or at least 6 months of storage at 25° C.; or after at least 6 months of storage at 25° C. and at least 18 months of storage at 5° C.

In one embodiment, the pharmaceutical premix formulation is stable for at least 3 months, at least 6 months, at least 12 months, at least 18 months, or at least 24 months of storage at about 25 degrees Celsius, e.g., in the sealed container system provided herein. In some embodiments, the pharmaceutical premix formulation is stable for at least 3 months, at least 6 months, at least 12 months, at least 18 months, or at least 24 months of storage at about 40 degrees Celsius, e.g., in the sealed container system provided herein. The formulation and the sealed container system provided herein can together confer long-term stability to the ready-to-use vasopressin premix formulation provided herein.

Parameters that can be used to assess stability of a formulation include, but are not limited to pH, percentage or amount of the active ingredient (e.g., vasopressin) remaining, percentage or amount of a lead impurity (e.g., Impurity N) or total impurities, visual appearance, particulate matter, level of bacterial endotoxins, sterility, and fill and air volume of a packaged container containing the formulation.

With respect to the long-term stability of the vasopressin formulations disclosed herein, degradation is a much more significant concern for lower concentration ready-to-use vasopressin formulations relative to higher or concentrated concentration formulations. Degradation of vasopressin is a significant issue as it can lead to vasopressin formulations with diminished potency, which can be particularly problematic when known dosage amounts are required to raise blood pressure in a subject. Thus, the long-term, stable storage of a ready-to-use vasopressin formulation that is achieved with the sealed container system and vasopressin formulations according to the present disclosure affords both clinicians and subjects with significant, practical benefits.

Parameters that can be used to assess stability of a formulation include, but are not limited to pH, percentage or amount of the active ingredient (e.g., vasopressin) remaining, percentage or amount of a lead impurity (e.g., Impurity N) or total impurities, visual appearance, particulate matter, level of bacterial endotoxins, sterility, and fill and air volume of a packaged container containing the formulation. For example, stability may be measured by the level of degradant over time. Impurities may be formed via degradation of one or more components of the composition. Sources of degradation include, but are not limited to, oxidation, racemization, visible light, ultraviolet light, moisture, heat, changes in pH, and composition component interactions.

As described above, stability of a pharmaceutical premix formulation described herein can be determined by assaying the level of degradant(s) over a period of time. A pharmaceutical premix formulation may be stable if t contains an amount of impurities within pharmaceutical permissible limits following storage at 25 degrees Celsius over six months or storage at 5 degrees Celsius over 24 months. In one embodiment, the stable premix formulation contains 4% or less degradant impurity N following 6 months or less or storage at 25 degrees Celsius. In one embodiment, the premix vasopressin formulation is stored in an intravenous bag.

An example of degradants of vasopressin is Related Compound N, as depicted in FIG. 1. Related Compound N is the sum of Related Compound N1 (the terminally deamidated modification, Gly9-OH vasopressin) and Related Compound N2 (a mixture of two other deamidations which can occur at either the Gln4 or the Asn5 amino acid residues). In some embodiments, deamidation is the only observed degradation mechanism of the vasopressin peptide at the conditions present within the premix formulation provided herein, and as such, the only impurity observed above the reporting threshold over the storage of the vasopressin premix formulation is Related Compound N. In some embodiments, the vasopressin premix formulation provided herein has no more than 4.0%, no more than 3.9%, no more than 3.8%, no more than 3.7%, no more than 3.6%, no more than 3.5%, no more than 3.4%, no more than 3.3%, no more than 3.2%, no more than 3.1%, no more than 3.0%, no more than 2.9%, no more than 2.8%, no more than 2.7%, no more than 2.6%, or no more than 2.5%, degradation product after certain period of shelf life (e.g., 3 months, 6 months, 9 months, 12 months, 15 months, 18 months, 21 months, or 24 months at 5° C., or 3 months or 6 months at 25° C., e.g., when stored in an intravenous bag). In other embodiments, the vasopressin premix formulation provided herein comprises has no more than 4.0%, no more than 3.9%, no more than 3.8%, no more than 3.7%, no more than 3.6%, no more than 3.5%, no more than 3.4%, no more than 3.3%, no more than 3.2%, no more than 3.1%, no more than 3.0%, no more than 2.9%, no more than 2.8%, no more than 2.7%, no more than 2.6%, or no more than 2.5%, Related Compound N over the storage period (e.g., 3 months, 6 months, 9 months, 12 months, 15 months, 18 months, 21 months, or 24 months at 5° C., or 3 months or 6 months at 25° C., e.g., when stored in an intravenous bag). The amounts recited in the tables in the Examples are also contemplated as being levels with respect to low levels of degradant which is representative of a stable vasopressin premix formulation.

Assays for determining levels of Related Impurity N are known in the art, including high performance liquid chromatography (HPLC). Examples of detection methods are also described in the Examples. In addition, methods for detecting impurities in a vasopressin formulation are described in PCT Publication WO 23/129844, U.S. application Ser. No. 18/069,198, and U.S. Pat. No. 9,375,478, which are each incorporated by reference herein.

Additionally or alternatively, stability of a pharmaceutical premix formulation can be, determined by percentage or amount of the active ingredient (e.g., vasopressin) remaining in the formulation. In one embodiment, the pharmaceutical premix formulation contains between about 88% and 110, about 89% and 110%, or 90% and 110% of the initial (labeled) amount of vasopressin after at least three months of storage at about 25 degrees Celsius, after at least six months of storage at about 25 degrees Celsius, after at least one year of storage at about 25 degrees Celsius, after at least three months of storage at about 5 degrees Celsius, after at least six months of storage at about 5 degrees Celsius, after at least one year of storage at about 5 degrees Celsius, or after at least two years of storage at about 5 degrees Celsius.

Additionally or alternatively, stability of a pharmaceutical premix formulation can be determined by changes in color, clarity, pH, and/or particulate matter of the formulation over time. In one embodiment, after certain period of shelf life (e.g., three months, six months, one year) at 25 degrees Celsius or at 5 degrees Celsius, the vasopressin premix formulation is a clear colorless solution, with color no more intense than purified water, and/or essentially free from visible particulate matter. In one embodiment, after certain period of shelf life (e.g., three months, six months, one year) at 25 degrees Celsius or at 5 degrees Celsius, the vasopressin premix formulation contains no more than 6000 particles that is 10 μm or greater in size per container (e.g., an about 100 mL container), and/or no more than 600 particles that are 25 μm or greater size per container, e.g., a 100 mL container. In one embodiment, after certain period of shelf life (e.g., three months, six months, one year) at 25 degrees Celsius or at 5 degrees Celsius, the pH of the vasopressin premix formulation remains within the predetermined range, such as within pH 3.6-4.0.

The pharmaceutical premix formulation of the disclosure has long term stability, e.g., the formulation is stable for at least 6 months at 25 degrees Celsius. In other embodiments, the pharmaceutical premix formulation is stable for 3 months at 25 degrees Celsius.

Advantageously, the ready-to-use vasopressin formulation demonstrates unexpected long-term stability at low vasopressin concentrations even when the formulation is free of a preservative. Thus, in certain embodiments, a pharmaceutical premix formulation of the disclosure comprising vasopressin is essentially free of a preservative. Examples of preservatives include, but are not limited to, sodium benzoate, EDTA, sorbic acid, and parabens. In certain embodiments, the pharmaceutical premix formulation is free of EDTA, e.g., is free of disodium EDTA.

Advantageously, the ready-to-use vasopressin formulation demonstrates unexpected long-term stability at low vasopressin concentrations even when the formulation is free of an antioxidant. The term "antioxidant," as used herein, refers to any antioxidant that can be typically be used in a parenteral formulation, but is not included in significant amounts in the ready-to-use vasopressin formulations described herein. Specific antioxidants that may be excluded from the ready-to-use vasopressin formulations described herein include sodium sulfite, sodium bisulfite, sodium metabisulfite, ascorbic acid, cysteine, as well as other antioxidants for parenteral formulations, and combinations thereof. In particular, it has been found that ascorbic acid should be avoided.

Sealed Container Systems

Also provided herein is a sealed container system for stable storage of a premix vasopressin formulation. The sealed container system can comprise a primary container comprising a premix vasopressin formulation comprising about 0.1 unit/mL to about 1 unit/mL vasopressin, about 8.5 mg/mL to about 9.5 mg/mL sodium chloride, about 2.5 mM to about 3.5 mM or about 280 μg/mL to about 400 μg/mL of a lactate salt, wherein the premix vasopressin formulation is an aqueous formulation and has a pH of about 3.1 to about 4.5, and wherein the primary container is a multi-layer plastic container comprising a layer of polyethylene, wherein the primary container is a bag, e.g., an intravenous (IV) bag having a volume of 50 mL to 500 mL. In certain embodiments, the premix vasopressin formulation also comprises a pH adjustor(s) which is sodium hydroxide and/or hydrochloric acid.

Table 1 describes one embodiment of the premix formulation of the invention.

TABLE 1

Example vasopressin premix formulation

| Component | Quality Standard | Function | Component Quality 20 U/100 mL[b] | 40 U/100 mL[b] |
|---|---|---|---|---|
| Vasopressin | USP | Active ingredient | 20 U/≈36.3 μg[a] | 40 U/≈72.6 μg[a] |
| Sodium Chloride | USP | Osmolarity adjuster | 900 mg | 900 mg |
| Sodium D,L-Lactate | USP | Buffer Agent | 0.336 g (3 mM) | 0 .336 g (3 mM) |
| Hydrochloric Acid | NF | pH adjuster | pH adjustment | pH adjustment |
| Sodium Hydroxide | NF | pH adjuster | pH adjustment | pH adjustment |
| Water for Injection | USP | Drug vehicle | QS | QS |

USP = United States Pharmacopeia;
QS = Quantity Sufficient;
NF = National Formulary
[a]Assumes a conversion rate of 551.19 Units/mg. Conversion rate is based on USP reference standard lot containing 1.68 mg and 926 USP Vasopressin units per vial.
[b]Volume: 100 mL; Fill volume: 103.5-106.5 mL.

TABLE 2

Example vasopressin premix formulation

| Component | Quality Standard | Component Quality 20 U/100mL | 40 U/100mL |
|---|---|---|---|
| Vasopressin | USP | 36.3 μg/100 mL (363 ng/ml)[a] | 72.6 μg/100 mL (726 ng/ml)[a] |
| Sodium Chloride | USP | 900 mg/100 mL (9 mg/mL) | 900 mg/100mL (9 mg/mL) |
| Sodium D,L-Lactate | USP | 33.6 mg/100 mL (336 μg/mL) | 33.6 mg/100 mL (336 μg/mL) |
| Hydrochloric Acid | NF | pH adjustment | pH adjustment |
| Sodium Hydroxide | NF | pH adjustment | pH adjustment |
| Water for Injection | USP | QS | QS |

USP = United States Pharmacopeia;
QS = Quantity Sufficient;
NF = National Formulary
[a]Assumes a conversion rate of 551.19 Units/mg. Conversion rate is based on USP reference standard lot containing 1.68 mg and 926 USP Vasopressin units per vial.

A system, as defined herein, comprises a primary container (e.g., an IV bag) and a premix vasopressin formation. The sealed container system may be connected to an infusion tube through which the premix vasopressin formulation contained in the system can be administered to a subject without dilution prior to administration.

The pharmaceutical premix vasopressin formulation may be contained in a flexible primary container, such as an IV bag. The primary container can hold a volume suitable for intravenous delivery. For example, the primary container may hold 50 mL to 500 mL of a formulation described herein. In one embodiment, the primary container holds a deliverable volume of about 100 mL of a pharmaceutical premix formulation described herein. In one embodiment, the intravenous bag contains 100 to 110 mL of formulation, about 100 mL, about 103.5 mL-106.5 mL, or about 105 mL. In one embodiment, the intravenous bag contains enough volume to deliver 100 mL of the premix vasopressin formulation to a human subject in need thereof. In certain embodiments where an intravenous bag is of sufficient volume to administer 100 ml of the premix formulation, the bag may have a volume limit of 110 mL, 109 mL, 108 mL, 107 mL, 106 mL, 105 mL, 104 mL, or 103 mL, or ranges thereof. In one embodiment, the vasopressin formulation is a sterile, aqueous solution of synthetic arginine vasopressin for intravenous administration. The formulation can be contained in a primary container holding 100 mL of a formulation containing 20 units (0.2 units/mL) or 40 units (0.4 units/mL) of vasopressin. In one embodiment, each 100 mL also contains 900 mg Sodium Chloride USP, 33.6 mg Sodium DL-Lactate USP, and Water for Injection, USP. pH may be adjusted with sodium hydroxide and/or hydrochloric acid. In certain embodiments, a premix formulation described herein has a pH of 3.6-4.0.

In one embodiment, a sealed container system comprises a 100 mL single dose primary container which comprises either 20 units vasopressin (0.2 units/mL) or 40 units vasopressin (0.4 units/mL) in a formulation described herein.

In certain embodiments the primary container in which the premix formulation is housed is a flexible container comprising multi-layers. In certain embodiments, the primary container is a multi-layer plastic bag for IV administration. The primary container can be aseptically filled. In certain embodiments, the primary container is a tri-laminate. In other embodiments, the primary container is a four layer film container.

In certain embodiments, the primary container is a flexible container which contains polyvinyl chloride (PVC) or di (2-ethylhexyl) phthalate (DEHP), or layers made of a combination of said compounds. Examples of PVC and/or DEHP containers are disclosed in U.S. Pat. Nos. 5,849,843 and 5,998,019, which are each hereby incorporated by reference in their entirety. Flexible bags suitable as primary containers include those also disclosed in US 2008/0249499, which is hereby incorporated by reference in its entirety.

An example of a primary container that can be used in the closed container system described herein is a GALAXY container (Baxter International Inc.). Other flexible bags, such as VIAFLO containers (Baxter International Inc.) and INTRAVIA containers (Baxter International Inc.) can also be used in the closed container system described herein.

In certain embodiments, the sealed container system provided herein further includes a secondary container containing the primary container therein. An oxygen scavenger can be optionally disposed between and enclosed by the secondary container. As described in further detail herein, the sealed container system disclosed herein can advantageously facilitate and thereby significantly increase long-term, stable storage of the ready-to-use vasopressin formulation.

An example of a container system that can be used to house the premix formulations provided herein is a GALAXY premix system (Baxter International Inc.). GALAXY is a multi-layered, plastic container closure system which provides stability for the premix vasopressin formulation described herein. A GALAXY premix system can be filled aseptically and the system need not undergo terminal sterilization, which is advantageous for storing formulations for which a terminal sterilization process is suitable (e.g., because the active ingredient is inactivated by terminal sterilization), such as peptide drug formulations including vasopressin formulations.

In one embodiment, the intravenous bag holding the premix, vasopressin formulation is aseptically filled, and does not undergo terminal sterilization.

In one embodiment, the primary container has a first flexible sheet layer and an opposing second flexible sheet layer. Each flexible sheet layer can have a multilayer sheeting, such as three or four layers, e.g., made of polyethylene (PE).

The primary container can further have a primary container seal disposed along a common peripheral edge of the first and second flexible sheet layers. The flexible bag, commonly referred to as an IV bag, may be formed by any of a number of methods, for example, by an exemplary form/fill/seal process where a sheet layer (or film) is aligned and then folded by a folding triangle. After that aligning and folding step, the film can be cut to allow the introduction of a port system (described below) between the two resulting facing films. The port system can then be automatically fed in place and welded between the two opposing faces of the folded film. By vertical welding the bottom part of the bag is formed and a hanger hole is punched. The side of the bag is formed by horizontal welding, while the solution for infusion is fed into the formed flexible bag. The upper horizontal welding also can form the lower side of the next bag. Finally, each bag is separated from the other during a sealing/cutting process. Thus, the flexible bag may be formed of a single sheet layer of flexible material, folded and sealed along the peripheral edges.

In other methods, two flexible sheets are joined at a top end and two side edges, i.e., when the two flexible sheets are placed in facing relationship they can be joined at their overlying/overlapping peripheral edges, while leaving an opening at a bottom end. The sealed top end and side edges, along with the open bottom end, are collectively referred to herein as the peripheral edges of the flexible bag. The top end includes a hanger aperture, which is preferably laterally offset from a central vertical axis of the flexible bag portion. The port system can then be fed in place and welded between the two opposing flexible sheets. Any other known method of bag manufacture, such as blow molding or vacuum forming, may also be used.

The primary container can include an administration port. In one embodiment, the primary container is a flexible bag with a single port adapted for fluid delivery (internally or externally), the single port comprising an administration port for delivering formulations comprising an oxygen-sensitive pharmaceutical compound, for example, the ready-to-use vasopressin formulations disclosed herein, to a subject via connection to an administration set. Because the primary container includes a ready-to-use formulation therein, the primary container according to this certain embodiment does not include a separate functioning "injection" or "reconstitution" port that allows a fluid to be added to the formulation of the primary container.

In one embodiment, the primary container can be disposed within and enclosed by a secondary container. The secondary container may be an overpouch container. Overpouches are flexible containers that can be used as secondary containers in the packaged, sealed container systems disclosed herein to store, protect, and transport the primary containers containing a formulation comprising an oxygen-sensitive pharmaceutical compound such as vasopressin therein. Overpouches can be provided by a third flexible sheet layer, an opposing fourth flexible sheet layer, and a seal disposed along a common peripheral edge of the third and fourth flexible sheet layers. (The first and second flexible sheet layers are contained in the primary container.)

The secondary overpouch container may, in certain embodiments, be optically transparent to enable visual inspection of the primary container and any other contents within the overpouch. It is also desirable for the overpouch container to be capable of withstanding autoclaving or other terminal sterilization process without causing the medical component therein to shrink/wrinkle and without becoming discolored and/or adhered to the medical component. Further, the layers of the overpouch (secondary) container can have a reduced water vapor transmission rate, such as a water vapor transmission rate of less than 5.0 $g/m^2/day$, less than 4.0 $g/m^2/day$, less than 3.0 $g/m^2/day$, less than 2.0 $g/m^2/day$, or less than 1.0 $g/m^2/day$.

The overpouch container may be an aluminum overpouch, a light absorbing polymeric overpouch, or a similar barrier structure. In one embodiment, the primary container is in fluid communication with any other contents of the overpouch secondary container.

In one embodiment, the overpouch secondary container comprises a top (third) flexible sheet layer comprising an amber transparent film and a bottom (fourth) flexible sheet layer comprising an opaque aluminum laminated foil. This type of secondary container can offer improved protection from light and is suited to contain a primary container containing a photo sensitive formulation. The top (third) flexible sheet layer of may be an amber transparent multilayer film to allow the contents within the secondary container, for example, any labeling on the primary container to be seen. The bottom (fourth) flexible sheet layer may be an opaque laminated foil comprising a metal foil, e.g., an aluminum foil. A seal is disposed along a common peripheral edge of the first and second flexible sheets.

In another embodiment, the overpouch secondary container comprises a top (third) flexible single layer sheet layer comprising a polymeric blend of a high density polyethylene and a surface enhancing polymer, an opposing bottom (fourth) flexible single layer sheet layer comprising a polymeric blend of a high density polyethylene and a surface enhancing polymer of an ethylene propylene diene terpolymer dispersed in a polyolefin matrix, and a seal disposed along a common peripheral edge of the top and bottom flexible sheets as disclosed in US 2006/0240204, which is hereby incorporated by reference in its entirety.

In specific embodiments, the secondary container provided herein for stable storage of a ready-to-use vasopressin formulation comprises the top (third) flexible sheet layer comprising a clear transparent film and the bottom (fourth) flexible sheet layer comprising a laminated aluminum foil.

An adhesive label can be applied on the exterior of the secondary container, e.g., on the aluminum foil (of the bottom flexible layer). Additionally or alternatively, the packaged, sealed container system can be labeled by stamp printing on the exterior of the secondary container.

In one embodiment, an oxygen scavenger (also referred to as oxygen absorber) is not included in the packaged, sealed container system provided herein. Alternatively, in one embodiment, an oxygen scavenger (or oxygen absorber) is disposed within and enclosed by the overpouch secondary container. A sachet located adjacent to the primary container and disposed within the secondary overpouch container may include the oxygen scavenger. The sachet (i.e., the bag) itself is porous and may comprise polyethylene materials. The oxygen scavenger may comprise iron powder, iron oxide powder, or a mixture thereof, for example, micronized iron. Other known oxygen scavengers may also be used. The oxygen scavenger is primarily included to absorb small amounts of oxygen that permeate through the secondary container during the shelf life of the drug product.

Thus, when a secondary container is included in the system, in certain embodiments, despite the primary and secondary containers being sealed, the fluid contents of the primary container may be considered to be in fluid communication with the contents of the secondary container, including the oxygen scavenger. Thus, the oxygen scavenger can be considered to be in fluid communication with the formulation of the primary container.

When formulations are provided in a packaged, sealed container system as described herein, the formulations described herein can be stable for a certain period of time. The ready-to-use formulations can be stable for at least 90 days, at least 120 days, at least 150 days, at least 180 days, and/or at least 1 year at 5° C. or 25° C., such that, for example, the vasopressin contained in the formulation retains at least about 88%, at least about 89%, at least about 90%, at least about 95%, and/or at least about 99% of the initial activity as measured by the initial and the final amounts of vasopressin.

Advantageously, the ready-to-use vasopressin formulation maintains long-term stability at low concentrations of vasopressin (e.g., stable for at least 6 months at 25 degrees Celsius) while being substantially free of an antioxidant or a preservative, particularly when packaged and sealed in the packaged, sealed container system described herein. It was unexpected that the vasopressin formulations according to the disclosure, particularly because of the very low concentrations of vasopressin suitable for direct parenteral administration to a subject, shows substantially equivalent, or even improved, stability as compared to the formulations with higher concentration vasopressin or with antioxidants or preservatives.

Procedures for filling the vasopressin formulation according to the invention in primary containers, and their subsequent processing are known in the art. Aseptic filling procedures are known and are often used to produce sterile pharmaceutical injectable drug products. Terminal sterilization, e.g., autoclaving, is conventionally used for sterilizing the formulation according to the invention. In specific embodiments, the container system provided herein (such as GALAXY system) is aseptically filled with the premix formulation that is heat sensitive, without undergoing terminal sterilization. In specific embodiments, the vasopressin premix formulation is aseptically filled into the container system provided herein, and no terminal sterilization is performed. Such system and process are advantageous for use with formulations for which terminal sterilization is not suitable (e.g., because the active ingredient is inactivated by terminal sterilization), including vasopressin formulations.

Sterile pharmaceutical formulations according to the present invention may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization or by being exposed to a peroxide bath, prior to filling. The primary container (bag) is then filled under aseptic conditions. The primary container is then optionally placed in a secondary container under aseptic conditions.

Sterilization can be conducted by, for example, by filtration through a bacteria retaining filter, by incorporating sterilizing agents into the compositions, and using other known techniques.

The sealed container system including the premix vasopressin formulation as disclosed herein may be stored at any suitable temperature, for example, at room temperature or at a low temperature, for example, at a temperature between about 5° C.

Therapeutics Uses of Vasopressin Pharmaceutical Premix Formulations

The system comprising vasopressin formulations described herein can be used, in particular, for increasing blood pressure in a human patient with vasodilatory shock who remains hypotensive despite fluids and catecholamines. In certain embodiments, the patient is an adult human.

The system described herein is used for parenteral administration, such as intravenous administration, of a vasopressin formulation and can be administered to the patient according to a certain unit per minute. In one embodiment, the vasopressin premix formulation provided herein is administered intravenously for post-cardiotomy shock at 0.03 to 0.1 units/minute. In one embodiment, the vasopressin premix formulation provided herein is administered intravenously for septic shock at 0.01 to 0.07 units/minute. In certain embodiments, the vasopressin premix formulation provided herein is titrated up by 0.005 units/minute at 10- to 15-minute intervals until the target blood pressure is reached in the human subject. In one embodiment, after target blood pressure has been maintained for 8 hours without the use of catecholamines, administration (e.g., injection) of the vasopressin premix formulation provided herein is tapered by 0.005 units/minute every hour as tolerated to maintain target blood pressure.

Vasopressin is a polypeptide hormone that causes contraction of vascular and other smooth muscles and antidiuresis. Vasopressin is used to increase blood pressure in adults with vasodilatory shock (e.g., post-cardiotomy or sepsis) who remain hypotensive despite fluids and catecholamines.

At therapeutic doses exogenous vasopressin elicits a vasoconstrictive effect in most vascular beds including the splanchnic, renal and cutaneous circulation. In addition, vasopressin at pressor doses triggers contractions of smooth muscles in the gastrointestinal tract mediated by muscular V1-receptors and release of prolactin and ACTH via V3 receptors. At lower concentrations typical for the antidiuretic hormone vasopressin inhibits water diuresis via renal V2 receptors. In addition, vasopressin has been demonstrated to cause vasodilation in numerous vascular beds that are mediated by V2, V3, oxytocin and purinergic P2 receptors.

In patients with vasodilatory shock, vasopressin in therapeutic doses increases systemic vascular resistance and mean arterial blood pressure and reduces the dose requirements for a catecholamine (e.g., norepinephrine, epinephrine). Vasopressin tends to decrease heart rate and cardiac output. The pressor effect is proportional to the infusion rate of exogenous vasopressin. The pressor effect reaches its peak within 15 minutes. After stopping the infusion the pressor effect fades within 20 minutes. There is no evidence for tachyphylaxis or tolerance to the pressor effect of vasopressin in patients.

In the formulations described herein, vasopressin plasma concentrations increases linearly with increasing infusion rates from 10 to 200 U/kg/min. Steady state plasma concentrations are achieved after 30 minutes of continuous intravenous infusion. In certain embodiments, the dose of vasopressin that is administered to the subject will be variable based on patient weight and patient response.

In one embodiment, provided herein is a method of increasing blood pressure in a subject (e.g., a human subject) in need thereof. The method comprises obtaining an intravenous bag comprising a ready-to-use, vasopressin formulation; and administering to the subject in need thereof, an effective amount of the vasopressin formulation by intravenous infusion, wherein the formulation is not diluted prior to administration to the subject. In one embodiment, the method comprises intravenously administering a therapeutically effective amount of the a premix vasopressin formulation in a sealed container system for stable storage of a pharmaceutical premix vasopressin formulation provided herein to the human subject via an infusion tube connected to the sealed container system without diluting the premix vasopressin formulation prior to administration to the human subject.

EXAMPLES

The following examples support the concept of an aqueous, pharmaceutical premix vasopressin formulation which is ready to use and does not require dilution. Further, the premix vasopressin formulations are stable in the sealed container system provided herein, including at room temperature. The examples support a product for treating hypotension in a human patient requiring vasopressin via intravenous infusion. The following examples are included for illustrative purposes only and are not intended to limit the scope of the invention.

Over time, and at an increasing rate with higher temperature, vasopressin slowly undergoes deamidation at one of three available sites on the peptide to produce impurities. These three deamidation degradants are collectively referred to as "Related Compound N" or "Impurity N" and are described in FIG. 1. Impurity N is the compound referred to throughout the examples in reference to the vasopressin degradation.

Example 1: Impact of pH on Vasopressin Premix Formulation Stability

The following studies examine the impact of pH on stability of a vasopressin premix formulation.

Experimental Design 1

A Design Of Experiments (DOE) approach was utilized to test formulation conditions. 1 U/mL vasopressin solutions in 0.9% sodium chloride and buffered with sodium lactate (at 0.3, 1.5, and 3.0 mM) to pHs 3.0, 3.4, 3.7, or 4.0 were formulated, as shown in Table 3. All of the samples were conditioned at 55° C. for approximately one week. Each formulation was sampled via the Cthulhu sampling system approximately every 8 hours for vasopressin assay and impurity analysis—Method A as described below. All of the solutions were measured for pH at the conclusion of one week of conditioning. The final pH and vasopressin assay values were used as dependent metrics to evaluate the stability of the formulation and in the Fusion software The buffer profile and the initial and final pH and vasopressin assay data are shown in Table 3. A target pH to prevent degradation of vasopressin was determined to be 3.65. There was no predicted difference in the performance between a solution buffered with 0.3 mM and 3.0 mM sodium lactate when conditioned for 1 week at 55° C.

TABLE 3 pH and vasopressin amount of DOE formulations before and after conditioning at 55° C. for one week

| Formulation No. | Lactate (mM) in formulation | Initial pH | Final pH | Vasopressin, % of initial amount |
|---|---|---|---|---|
| 1 | 0.3 | 3.70 | NA[1] | NA[1] |
| 2 | 1.5 | 3.41 | 3.69 | 92.93 |
| 3 | 0.3 | 3.99 | 4.32 | 91.64 |
| 4 | 1.5 | 2.99 | 3.01 | 88.91 |
| 5 | 1.5 | 3.40 | NA[1] | NA[1] |
| 6 | 3.0 | 3.70 | 3.72 | 95.42 |
| 7 | 0.3 | 4.00 | 4.11 | 94.38 |
| 8 | 0.3 | 3.01 | 3.01 | 89.40 |
| 9 | 0.3 | 3.40 | 3.41 | 94.57 |
| 10 | 3.0 | 2.99 | 3.00 | 89.14 |
| 11 | 3.0 | 2.99 | 2.99 | 89.66 |
| 12 | 3.0 | 3.99 | 4.01 | 94.82 |

[1]Due to a system error, final measurements were not taken for these formulations, and these formulations were not used for the stability analysis.

Experimental Design 2

The next study was performed to determine the impact of sodium lactate buffer concentration. Solutions of 0.1, 0.2, and 0.4 U/mL vasopressin in 0.9% sodium chloride were buffered with sodium lactate at sodium lactate concentrations of 0.05, 0.3, 0.1, 0.2, 0.3, 0.6, 1.2, and 3.0 mM at a target pH of 3.65. The vasopressin and sodium lactate concentrations in each formulation are shown in Tables 4 and 5. Samples were conditioned at 55° C. for approximately one week. Each formulation was sampled via the Cthulhu sampling system approximately every 8 hours for vasopressin assay and impurity analysis—Method B as described below.

As shown in Table 4, all samples, with the exception of formulation 2 (vasopressin 0.1 U/mL, lactate 0.3 mM), maintained the target pH within the expected method variability.

Figure 3:
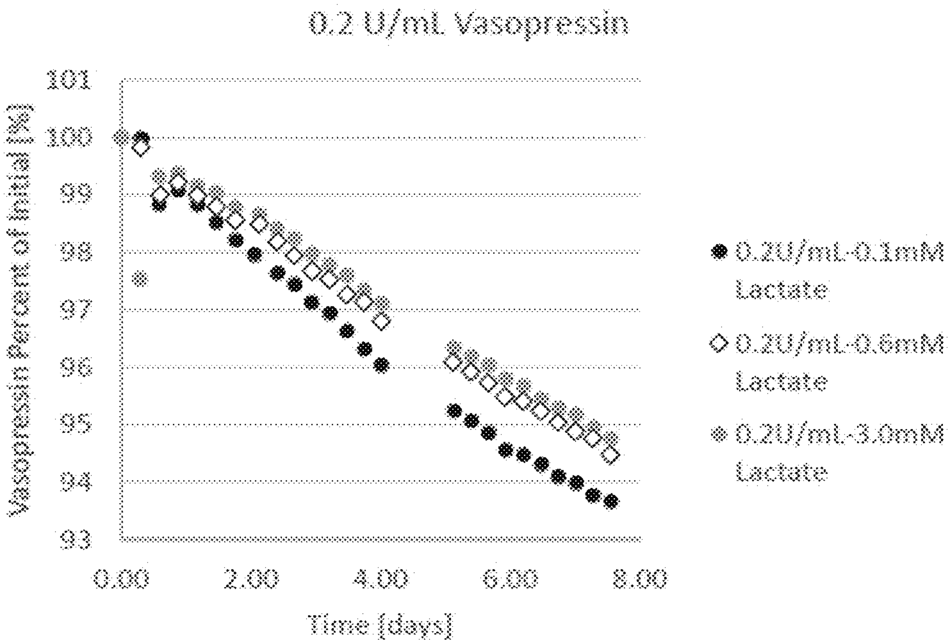
FIG. 3 depicts the amount of vasopressin (% of initial) in the 0.2 U/mL vasopressin premix formulations with varied lactate concentrated as indicated.
Figure 4:
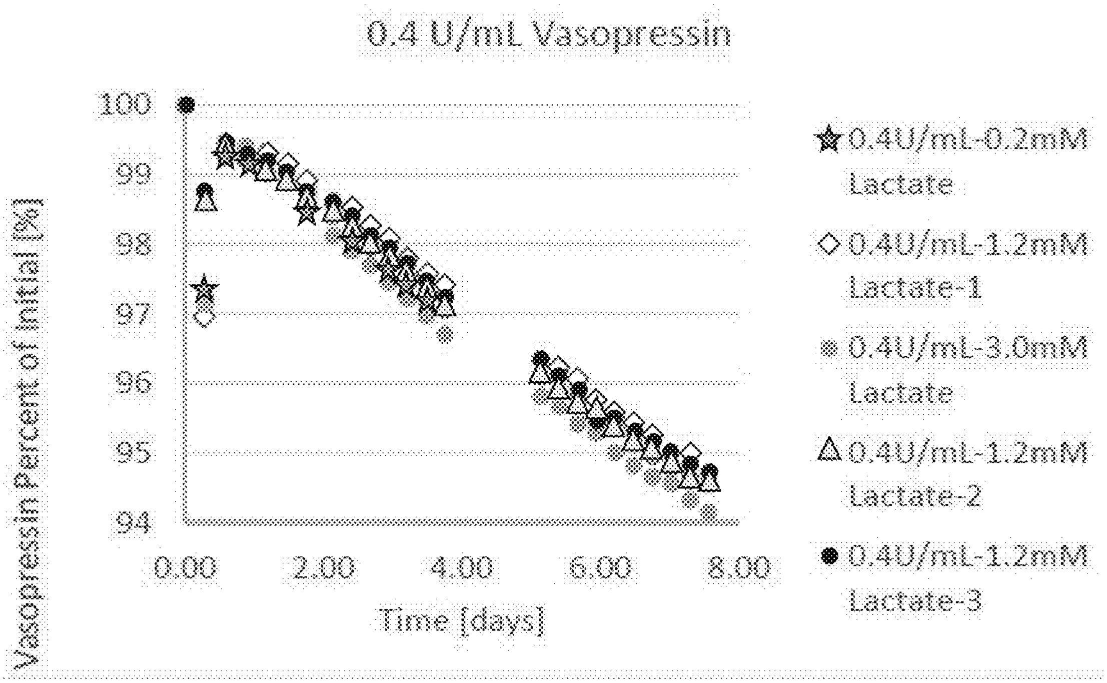
FIG. 4 depicts the amount of vasopressin (% of initial) in the 0.4 U/mL vasopressin premix formulations with varied lactate concentrated as indicated.

As shown in FIGS. 2 and 3, the vasopressin degradation rate, observed by plotting the vasopressin values as a function of time, decreased as a function of increasing lactate concentration when the vasopressin concentration was 0.1 U/mL or 0.2 U/mL. As shown in FIG. 4, at 0.4 U/mL, there was not a strong effect of lactate concentration on the vasopressin degradation rate. In sum, among the lactate concentrations tested, 3.0 mM lactate provided the most protective effect against vasopressin degradation for 0.1 U/mL, 0.2 U/mL, or 0.4 U/mL vasopressin formulations.

TABLE 4

Initial and final pH values of lactate buffered formulations, 55° C. storage for one week

| Formulation No. | Vasopressin Concentration [U/mL] | Lactate Concentration [mM] | Initial pH | Final pH |
|---|---|---|---|---|
| 1 | 0.1 | 0.05 | 3.61 | NA[a] |
| 2 | 0.1 | 0.3 | 3.60 | 3.67 |
| 3 | 0.1 | 3.0 | 3.70 | 3.70 |
| 4 | 0.2 | 0.1 | 3.67 | 3.69 |
| 5 | 0.2 | 0.6 | 3.63 | 3.65 |
| 6 | 0.2 | 3.0 | 3.65 | 3.65 |
| 7 | 0.4 | 0.2 | 3.60 | 3.63 |
| 8 | 0.4 | 1.2 | 3.66 | 3.68 |
| 9 | 0.4 | 3.0 | 3.64 | 3.66 |
| 10 | 0.4 | 1.2 | 3.61 | 3.64 |
| 11 | 0.4 | 1.2 | 3.65 | 3.66 |

[a]Due to a system error, a final measurement was not taken for formulation 1.

Experimental Design 3

This study tested the effect of racemic sodium lactate on the stability of vasopressin formulations. 0.2 and 0.4 U/mL vasopressin in 0.9% sodium chloride and buffered with 3.0 mM lactate, and 0.2 U/mL vasopressin in 0.9% sodium chloride and buffered with 0.6 mM lactate, all to a target pH of 3.65 were formulated. All three solutions were formulated twice, once with sodium D-lactate and once with sodium D,L-lactate. All of the samples were conditioned at 55° C. for 6 days. Each formulation was sampled at time 0, 3 days, and 6 days for vasopressin assay—Method B as described below.

Table 5 shows the amount of vasopressin degradation calculated as the percent change seen in assay value from time 0 after 3 and 6 days of conditioning at 55° C. As shown in Table 5, for all three formulations tested, the formulation buffered by D-lactate degraded less than the formulation buffered by D,L-lactate. However, the differences between the two lactate forms were relatively small, and decreased over time, with smaller differences measured after 6 days of conditioning than after 3 days. After 6 days of conditioning, the largest difference in degradation observed between the two buffers was 1.06%. The results demonstrate that the D,L-lactate, in addition to D-lactate, would be an effective buffer for a vasopressin formulation.

TABLE 5

Vasopressin degradation in D-lactate and D,L-lactate formulations

| Formulation | 3 Day % difference in vasopressin value from initial | | 6 Day % difference in vasopressin value from initial | |
|---|---|---|---|---|
| (vasopressin, lactate) | D | D, L | D | D, L |
| 0.2 U/mL, 0.6 mM | −1.97% | −2.62% | −4.90% | −5.29% |
| 0.2 U/mL, 3.0 mM | −0.79% | −3.18% | −4.07% | −5.13% |
| 0.4 U/mL, 3.0 mM | −0.88% | −1.83% | −3.68% | −4.38% |

Summary

In conclusion, the studies in Example 1 demonstrated that 3.0 mM lactate provided less degradation of 0.1 U/mL or 0.2 U/mL vasopressin than 1.2 mM, 0.6 mM, 0.3 mM, 0.1 mM, or 0.05 mM lactate. Sodium D,L-lactate was comparative to sodium D-lactate in protecting the vasopressin from degradation. The DOE study identified a target formulation pH of 3.65.

Example 2: Long Term Stability of Vasopressin Premix Formulations in a Sealed Plastic Container System The following example describes studies that evaluated the stability of various formulations having vasopressin concentrations 0.2 U/mL and 0.4 U/mL. In particular, the study examined whether the tested formulations could sustain a refrigerated shelf life of 24 months in a plastic, sealed container system.

Experimental Design

Vasopressin was added to deionized water. Sodium chloride and sodium lactate were then added, followed by worst-case GALAXY residuals (i.e., chemical entities that represent residuals of the GALAXY manufacturing process). The pH was adjusted to 3.5, 3.65, or 3.8 as appropriate using 1.0N hydroxy chloride. Formulations were filtered through a 0.2 μm Nylon 66 capsule filter using a peristaltic pump and units were filled using a repeater pump after discarding the first 500 mL of solution.

Samples were characterized by visual inspection, vasopressin assay and related compounds (impurities) (using Method B above), pH, subvisible particulate matter, color, and osmolality at 0 month, 1 week, 1.5 months, 3 months, 6 months, 10 months, 13 months, 18 months, and 24 months of 5° C. storage (refrigerated, long term storage condition) and at 1.5 and 3 months of 25° C. storage (room temperature, short term storage condition). One combination condition of 12 months of 5° C. storage plus 1 month of 25° C. storage was also conducted. The sample groups were 0.2 U/mL and 0.4 U/mL vasopressin formulations with 3 mM sodium lactate buffer, formulated at pH values of 3.5, 3.65, and 3.8, all in GALAXY PL2501 100 mL containers, and a glass control at pH 3.65. A low lactate sample group was also created, with 0.2 U/mL vasopressin and 0.6 mM sodium lactate buffer. All samples used 0.9% sodium chloride as a tonicity adjustor. All test formulations were spiked with chemical entities that represent residuals of the GALAXY manufacturing process, at the following concentrations: 200 ppb of hydrogen peroxide, 10 ppm of sodium acid pyrophosphate, and 10 ppm of sodium dihydrogen phosphate.

Results

The subvisible particulate matter counts were near zero for all timepoints tested, confirming no particulate matter formed in this formulation and container closure system. Visual inspection similarly showed that environmental fibers and particles were common in glass samples and very rarely found in filled GALAXY containers.

Osmolarity and color were measured at the final timepoint. The color was NMT BY5 in all formulations after 24 month at 5° C. storage, and NMT BY 7 after 12 month at 5° C. and 1 month at 25° C. The values for the osmolality for the pH 3.5, 3.65, 3.8 GALAXY and pH 3.65 glass samples were 301, 295, 302, and 296 mOsm/kg, respectively. These are near the target of 300 mOsm/kg and within the desired range of 270-330 mOsm/kg.

As shown in Tables 6 and 7, the pH values were stable over time, with no change occurring at up to 24 months of 5° C. storage (Table 6) or up to 3 months of 25° C. storage (Table 7).

TABLE 6 pH, 5° C. storage

| Formulation/Condition | 0M | 1.5M | 3M | 6M | 10M | 13M | 18M | 24M |
|---|---|---|---|---|---|---|---|---|
| 0.2 U/mL vasopressin pH 3.5 3 mM lactate in GALAXY | 3.50 | 3.52 | 3.51 | 3.50 | 3.49 | — | 3.51 | 3.50 |
| 0.2 U/mL vasopressin pH 3.65 3 mM lactate in GALAXY | 3.69 | 3.70 | 3.69 | 3.67 | 3.67 | — | 3.68 | 3.68 |
| 0.2 U/mL vasopressin pH 3.8 3 mM lactate in GALAXY | 3.79 | 3.82 | 3.82 | 3.79 | 3.79 | 3.83 | 3.82 | 3.81 |
| 0.2 U/mL vasopressin pH 3.65 3 mM lactate in glass container | 3.68 | 3.69 | 3.69 | 3.66 | 3.65 | — | 3.67 | 3.68 |

TABLE 6-continued

| pH, 5° C. storage | | | | | | | | |
|---|---|---|---|---|---|---|---|---|
| Formulation/Condition | 0M | 1.5M | 3M | 6M | 10M | 13M | 18M | 24M |
| 0.2 U/mL vasopressin pH 3.65 0.6 mM lactate in GALAXY | 3.66 | 3.68 | 3.68 | — | — | — | — | — |
| 0.4 U/mL vasopressin pH 3.5 3 mM lactate in GALAXY | 3.51 | 3.49 | 3.46 | 3.46 | 3.46 | — | 3.47 | 3.48 |
| 0.4 U/mL vasopressin pH 3.65 3 mM lactate in GALAXY | 3.62 | 3.66 | 3.64 | 3.65 | 3.63 | — | 3.65 | 3.63 |
| 0.4 U/mL vasopressin pH 3.8 3 mM lactate in GALAXY | 3.79 | 3.80 | 3.81 | 3.80 | 3.78 | 3.84 | 3.81 | 3.80 |

TABLE 7

| pH, 25° C. storage | | | |
|---|---|---|---|
| Formulation/Condition | 0M | 1.5M | 3M |
| 0.2 U/mL vasopressin pH 3.5 3 mM lactate in GALAXY | 3.50 | 3.52 | 3.52 |
| 0.2 U/mL vasopressin pH 3.65 3 mM lactate in GALAXY | 3.69 | 3.69 | 3.69 |
| 0.2 U/mL vasopressin pH 3.8 3 mM lactate in GALAXY | 3.79 | 3.82 | 3.82 |
| 0.2 U/mL vasopressin pH 3.65 3 mM lactate in glass container | 3.68 | 3.69 | 3.70 |
| 0.2 U/mL vasopressin pH 3.65 0.6 mM lactate in GALAXY | 3.66 | 3.68 | 3.66 |
| 0.4 U/mL vasopressin pH 3.5 3 mM lactate in GALAXY | 3.51 | 3.49 | 3.50 |

TABLE 7-continued

| pH, 25° C. storage | | | |
|---|---|---|---|
| Formulation/Condition | 0M | 1.5M | 3M |
| 0.4 U/mL vasopressin pH 3.65 3 mM lactate in GALAXY | 3.62 | 3.66 | 3.67 |
| 0.4 U/mL vasopressin pH 3.8 3 mM lactate in GALAXY | 3.79 | 3.81 | 3.82 |

As shown in Tables 8 and 9, the vasopressin degradation was minimal at 5° C. over 24 months of storage. A tendency for the pH 3.5 (lowest) formulations to have slightly worse performance was also noted. The 25° C. storage data showed up to about 9% assay loss at 3 months of 25° C. storage, with significant variability of the data.

TABLE 8

| Vasopressin, % label claim, 5° C. storage | | | | | | | | |
|---|---|---|---|---|---|---|---|---|
| Formulation/Condition | 0M | 1.5M | 3M | 6M | 10M | 13M | 18M | 24M |
| 0.2 U/mL vasopressin pH 3.5 3 mM lactate in GALAXY | 100.5 | 104.4 | 102.1 | 99.9 | 101.3 | — | 99.6 | 98.7 |
| 0.2 U/mL vasopressin pH 3.65 3 mM lactate in GALAXY | 90.1 | 101.4 | 100.2 | 98.6 | 99.0 | — | 97.9 | 96.8 |
| 0.2 U/mL vasopressin pH 3.8 3 mM lactate in GALAXY | 93.1 | 104.1 | 102.5 | 102.3 | 102.5 | 100.5 | 99.1 | 102.7 |
| 0.2 U/mL vasopressin pH 3.65 3 mM lactate in glass container | 99.7 | 103.0 | 99.8 | 100.6 | 100.0 | — | 99.2 | 97.8 |
| 0.2 U/mL vasopressin pH 3.65 0.6 mM lactate in GALAXY | 98.9 | 102.8 | 99.6 | — | — | — | — | — |
| 0.4 U/mL vasopressin pH 3.5 3 mM lactate in GALAXY | 95.4 | 96.0 | 96.5 | 94.9 | 97.3 | — | 96.1 | 98.9 |
| 0.4 U/mL vasopressin pH 3.65 3 mM lactate in GALAXY | 97.8 | 101.3 | 98.3 | 98.3 | 99.5 | — | 98.2 | 99.6 |
| 0.4 U/mL vasopressin pH 3.8 3 mM lactate in GALAXY | 98.5 | 101.4 | 98.0 | 99.9 | 99.8 | 99.0 | 97.9 | 100.0 |

TABLE 9

| Vasopressin, % label claim, 25° C. storage | | | | |
|---|---|---|---|---|
| Formulation/Condition | 0M | 1.5M | 3M | 12M 5° C. + 1M 25° C. |
| 0.2 U/mL vasopressin pH 3.5 3 mM lactate in GALAXY | 100.5 | 99.0 | 98.8 | 99.8 |
| 0.2 U/mL vasopressin pH 3.65 3 mM lactate in GALAXY | 90.1 | 97.0 | 97.6 | 96.9 |
| 0.2 U/mL vasopressin pH 3.8 3 mM lactate in GALAXY | 93.1 | 100.2 | 100.9 | 100.7 |
| 0.2 U/mL vasopressin pH 3.65 3 mM lactate in glass | 99.7 | 99.2 | 91.0 | 98.4 |
| 0.2 U/mL vasopressin pH 3.65 0.6 mM lactate in GALAXY | 98.9 | 98.9 | 97.5 | — |
| 0.4 U/mL vasopressin pH 3.5 3 mM lactate in GALAXY | 95.4 | 95.1 | 94.8 | 96.5 |
| 0.4 U/mL vasopressin pH 3.65 3 mM lactate in GALAXY | 97.8 | 95.2 | 91.1 | 98.8 |
| 0.4 U/mL vasopressin pH 3.8 3 mM lactate in GALAXY | 98.5 | 97.8 | 90.9 | 98.6 |

For related compounds (impurities), as shown in Tables 10 and 11, trends were observed that echoed the vasopressin assay results. As shown in Tables 10 and 11, minimal growth of impurities occurred after 24 months of 5° C. storage or 12 months at 5° C. and 1 month at 25° C., and the pH 3.8 formulations seemed to have the best performance compared to the pH 3.5 and 3.65 formulations. As shown in Table 11, minimal growth of impurities occurred after 3 months of 25° C. storage in the pH 3.8 formulations, whereas up to 2% increase in related compounds was observed in the pH 3.5 and 3.65 formulations.

The only related compound of note was the co-eluting peak labelled Impurity N (Related Compound N), at relative retention time 1.04-1.05. The other related compounds seen in chromatograms were labeled Related Compound 5, with a relative retention time of 1.01-1.04 and ability to be separated from the vasopressin main peak, and Related Compound 7, with a relative retention time of 1.08-1.10. Neither of these two impurities grew with time or higher temperature conditioning when measuring samples at pH 3.8. Accordingly, Impurity N had good mass balance with the vasopressin loss.

TABLE 10

| Vasopressin related compounds, %, 5° C. storage | | | | | | | | |
|---|---|---|---|---|---|---|---|---|
| Formulation/Condition | 0M | 1.5M | 3M | 6M | 10M | 13M | 18M | 24M |
| 0.2 U/mL vasopressin pH 3.5 3 mM lactate in GALAXY | 2.0 | 2.2 | 1.8 | 1.0 | 0.5 | — | 1.3 | 1.6 |
| 0.2 U/mL vasopressin pH 3.65 3 mM lactate in GALAXY | 1.4 | 2.0 | 1.7 | 0.9 | 0.5 | — | 1.3 | 3.4 |
| 0.2 U/mL vasopressin pH 3.8 3 mM lactate in GALAXY | 2.1 | 2.0 | 2.1 | 0.7 | 0.7 | NMT 0.50% | 0.7 | 0.8 |
| 0.2 U/mL vasopressin pH 3.65 3 mM lactate in glass | 1.4 | 1.9 | 1.8 | 0.5 | 0.6 | — | 0.8 | 1.1 |
| 0.2 U/mL vasopressin pH 3.65 0.6 mM lactate in GALAXY | 2.3 | 2.0 | 1.7 | 1.8 | — | — | — | — |
| 0.4 U/mL vasopressin pH 3.5 3 mM lactate in GALAXY | 2.1 | 2.0 | 2.0 | 0.9 | 0.9 | — | 1.4 | 1.7 |
| 0.4 U/mL vasopressin pH 3.65 3 mM lactate in GALAXY | 2.2 | 1.9 | 1.7 | 0.6 | 0.7 | — | 0.9 | 1.1 |
| 0.4 U/mL vasopressin pH 3.8 3 mM lactate in GALAXY | 2.4 | 1.7 | 1.8 | 0.6 | 0.6 | NMT 0.50% | 0.7 | 0.8 |

TABLE 11

| Vasopressin related compounds, %, 25° C. storage | | | | |
|---|---|---|---|---|
| Formulation/Condition | 0M | 1.5M | 3M | 12M 5° C. + 1M 25° C. |
| 0.2 U/mL vasopressin pH 3.5 3 mM lactate in GALAXY | 2.0 | 2.3 | 3.9 | 1.6 |
| 0.2 U/mL vasopressin pH 3.65 3 mM lactate in GALAXY | 1.4 | 1.9 | 3.4 | 0.9 |
| 0.2 U/mL vasopressin pH 3.8 3 mM lactate in GALAXY | 2.1 | 1.9 | 3.0 | 0.8 |
| 0.2 U/mL vasopressin pH 3.65 3 mM lactate in glass | 1.4 | 1.7 | 2.8 | 0.9 |
| 0.2 U/mL vasopressin pH 3.65 0.6 mM lactate in GALAXY | 2.3 | 2.0 | 3.0 | — |
| 0.4 U/mL vasopressin pH 3.5 3 mM lactate in GALAXY | 2.1 | 5.0 | 4.0 | 1.5 |
| 0.4 U/mL vasopressin pH 3.65 3 mM lactate in GALAXY | 2.2 | 2.1 | 3.4 | 1.0 |
| 0.4 U/mL vasopressin pH 3.8 3 mM lactate in GALAXY | 2.4 | 1.7 | 3.0 | 0.7 |

In conclusion, this study demonstrates stability of the vasopressin premix formulation through a 24 month shelf life at 5° C., as no significant loss of assay, growth of impurities, change in pH, color, particulate matter, or osmolality were found. Suitability of vasopressin concentration of either 0.2 U/mL or 0.4 U/mL, the use of 0.9% sodium chloride as a tonicity adjustor, the use of 3 mM lactate as the buffering agent, and the use of a sealed container system such as a GALAXY container, were all confirmed as a result of the successful testing.

Example 3: Long Term Stability of Vasopressin Premix Formulations

The following example provides stability of vasopressin premix formulations (i) produced by conducting the mixing and filling at 100 L), (ii) over a wide range of pH, and (iii) after long periods of storage at 25° C.

Experimental Design

The following test and control formulations were prepared and studied: vasopressin concentration was either 0.2 U/mL or 0.4 U/mL; 0.9% sodium chloride was used as a tonicity adjustor; and the buffer system was 3 mM sodium lactate. Test articles were each 100 mL vasopressin premix formulations in a GALAXY bag, manually filled from the 100 L batch with a repeater pump from a mix tank through a 0.2 μm nylon-6,6 filter. The pH of the formulation was adjusted to either 3.4, 3.65, or 3.9.

Samples were characterized by visual inspection, vasopressin assay and related compounds (using Method B below), pH, subvisible particulate matter, color, and osmolality at 0, 3, 9, 12, 18, and 24 months of 5° C. storage and at 0, 1, 2, 3, 9, 12, 18, and 24 months of 25° C. storage. Samples were also characterized after 3 months of 30° C. storage and after 1 month of 40° C. storage.

Results

The stability of the formulation pH was observed. As shown in Tables 12 and 13, the 3 mM lactate buffer effectively maintained the pH over both 24 months of 5° C. storage as well as 12 months of 25° C. storage. Even 24 months of 25° C. storage showed only a modest decrease in the formulation pH.

TABLE 12

| pH, 5° C. Storage | | | | | | |
|---|---|---|---|---|---|---|
| Condition | 0M | 3M | 9M | 12M | 18M | 24M |
| 0.2 U/mL vasopressin, pH 3.4 | 3.36 | 3.37 | — | — | — | 3.25 |
| 0.2 U/mL vasopressin, pH 3.65 | 3.63 | 3.63 | — | — | 3.59 | 3.54 |
| 0.2 U/mL vasopressin, pH 3.9 | 3.85 | 3.87 | 3.9 | 3.89 | 3.83 | 3.77 |
| 0.4 U/mL vasopressin, pH 3.4 | 3.4 | 3.42 | — | — | — | 3.30 |
| 0.4 U/mL vasopressin, pH 3.65 | 3.62 | 3.65 | — | — | 3.60 | 3.53 |
| 0.4 U/mL vasopressin, pH 3.9 | 3.89 | 3.92 | 3.95 | 3.91 | 3.88 | 3.81 |

TABLE 13

| pH, 25° C. Storage | | | | | | | | |
|---|---|---|---|---|---|---|---|---|
| Condition | 0M | 1M | 2M | 3M | 9M | 12M | 18M | 24M |
| 0.2 U/mL vasopressin, pH 3.4 | 3.36 | 3.33 | 3.39 | 3.37 | — | — | — | 3.28 |
| 0.2 U/mL vasopressin, pH 3.65 | 3.63 | 3.62 | 3.67 | 3.65 | — | — | 3.60 | 3.55 |
| 0.2 U/mL vasopressin, pH 3.9 | 3.85 | 3.85 | 3.90 | 3.87 | 3.89 | 3.89 | 3.82 | 3.78 |
| 0.4 U/mL vasopressin, pH 3.4 | 3.40 | 3.37 | 3.44 | 3.41 | — | — | — | 3.30 |
| 0.4 U/mL vasopressin, pH 3.65 | 3.62 | 3.62 | 3.67 | 3.64 | — | — | 3.59 | 3.55 |
| 0.4 U/mL vasopressin, pH 3.9 | 3.89 | 3.91 | 3.94 | 3.93 | 3.94 | 3.94 | 3.88 | 3.83 |

The vasopressin assay data showed stability over 24 months. As shown in Table 14, at 5° C. storage, minimal loss of vasopressin occurred over 24 months. As shown in Table 15, at 25° C. storage, the vasopressin loss exhibited a strong pH dependence, with the most loss occurring at pH 3.4 and the least at pH 3.9. At pH 3.9, the total vasopressin loss was about 4.4% after 12 months of 25° C. storage and 9.5% after 24 months of 25° C. storage. Storage for 3 months at 30° C. produced about 2.5% vasopressin loss, and storage for 1M at 40° C. produced about 0.8% assay loss.

TABLE 14

| Vasopressin, % label claim, 5° C. Storage | | | | | | |
|---|---|---|---|---|---|---|
| Condition | 0M | 3M | 9M | 12M | 18M | 24M |
| 0.2 U/mL vasopressin, pH 3.4 | 99.5 | 98.3 | — | 100.0 | — | 98.3 |
| 0.2 U/mL vasopressin, pH 3.65 | 99.4 | 99.0 | — | 100.4 | 99.0 | 99.5 |
| 0.2 U/mL vasopressin, pH 3.9 | 99.7 | 98.0 | 100.9 | 101.2 | 100.2 | 99.1 |
| 0.4 U/mL vasopressin, pH 3.4 | 97.1 | 97.3 | — | 100.5 | — | 98.6 |

TABLE 14-continued

| Vasopressin, % label claim, 5° C. Storage | | | | | | |
|---|---|---|---|---|---|---|
| Condition | 0M | 3M | 9M | 12M | 18M | 24M |
| 0.4 U/mL vasopressin, pH 3.65 | 95.7 | 98.5 | — | 101.4 | 101.4 | 100.0 |
| 0.4 U/mL vasopressin, pH 3.9 | 98.2 | 98.0 | 101.3 | 101.2 | 102.5 | 99.9 |

TABLE 15

| Vasopressin, % label claim, 25° C. Storage | | | | | | | | |
|---|---|---|---|---|---|---|---|---|
| Condition | 0M | 1M | 2M | 3M | 9M | 12M | 18M | 24M |
| 0.2 U/mL vasopressin, pH 3.4 | 99.5 | 101.4 | 97.2 | 96.7 | — | 89.9 | — | 79.0 |
| 0.2 U/mL vasopressin, pH 3.65 | 99.2 | 102.1 | 97.2 | 98.4 | — | 94.2 | 90.2 | 86.5 |
| 0.2 U/mL vasopressin, pH 3.9 | 99.7 | 101.9 | 97.5 | 99.5 | 96.7 | 95.3 | 92.8 | 90.2 |
| 0.4 U/mL vasopressin, pH 3.4 | 97.2 | 101.6 | 96.1 | 97.2 | — | 90.3 | — | 82.0 |
| 0.4 U/mL vasopressin, pH 3.65 | 95.7 | 102.6 | 97.6 | 99.0 | — | 94.4 | 92.6 | 88.4 |
| 0.4 U/mL vasopressin, pH 3.9 | 98.2 | 102.2 | 97.6 | 99.3 | 97.7 | 96.0 | 96.4 | 90.8 |

Table 16 and Table 17 show the results for total related compounds over time at 5° C. and 25° C. storage conditions. The related compounds data followed similar trends to Example 2. The only impurity that grew with time and temperature (more at 25° C. than at 5° C.) was the co-eluting peak for Impurity N, which had good mass balance with the vasopressin assay loss, suggesting that it is the primary degradant of vasopressin. The Impurity N peak at retention time ~14.20 minutes emerged from the baseline and grew slightly over time.

The other related compounds seen in the chromatogram were labeled Related Compound 5, with a relative retention time of 1.01-1.04 and ability to be separated from the vasopressin main peak, and Related Compound 7, with a relative retention time of 1.08-1.10. Neither of these two impurities grew with time or higher temperature conditioning when measuring samples at pH 3.9. For all pH 3.9 data, the total related compounds and the total impurity N values were the same. The increase in the total related compounds amount over 24 months was least at pH 3.9, followed by pH 3.64, and most at pH 3.4, in both at 5° C. and 25° C.

TABLE 16

| Vasopressin related compounds, %, 5° C. Storage | | | | | | |
|---|---|---|---|---|---|---|
| Condition | 0M* | 3M* | 9M | 12M | 18M | 24M |
| 0.2 U/mL vasopressin, pH 3.4 | 0.1 | 1.3 | — | 1.1 | — | 3.5 |
| 0.2 U/mL vasopressin, pH 3.65 | 1.9 | 1.4 | — | 0.5 | 0.8 | 1.3 |
| 0.2 U/mL vasopressin, pH 3.9 | 2.3 | 1.2 | 0.3 | 0.2 | 0.4 | 0.5 |
| 0.4 U/mL vasopressin, pH 3.4 | 1.0 | 1.1 | — | 0.9 | — | 2.2 |
| 0.4 U/mL vasopressin, pH 3.65 | 3.4 | 1.0 | — | 0.5 | 0.8 | 0.9 |
| 0.4 U/mL vasopressin, pH 3.9 | 4.0 | 0.7 | 0.3 | 0.2 | 0.4 | 0.5 |

*At the 0M and 3M timepoints, a preliminary method was used to measure related compounds and these data are not reliable.

TABLE 17

| Vasopressin related compounds, %, 25° C. Storage | | | | | | | | |
|---|---|---|---|---|---|---|---|---|
| Condition | 0M* | 1M* | 2M* | 3M* | 9M | 12M | 18M | 24M |
| 0.2 U/mL vasopressin, pH 3.4 | 0.1 | 1.5 | 1.9 | 3.7 | — | 12.8 | — | 23.3 |
| 0.2 U/mL vasopressin, pH 3.65 | 1.9 | 1.1 | 1.3 | 2.5 | — | 6.7 | 9.3 | 12.8 |
| 0.2 U/mL vasopressin, pH 3.9 | 2.3 | 1.0 | 0.8 | 1.9 | 2.6 | 3.6 | 5.5 | 7.6 |
| 0.4 U/mL vasopressin, pH 3.4 | 1.0 | 1.3 | 2.1 | 3.5 | — | 11.5 | — | 20.5 |
| 0.4 U/mL vasopressin, pH 3.65 | 3.4 | 1.1 | 1.2 | 2.3 | — | 6.4 | 8.5 | 12.3 |
| 0.4 U/mL vasopressin, pH 3.9 | 4.0 | 0.8 | 0.7 | 1.4 | 2.4 | 3.2 | 4.6 | 6.3 |

*At the 0M and 3M timepoints, a preliminary method was used to measure related compounds and these data are not reliable.

In conclusion, the pH trend of the 25° C., 30° C., and 40° C. data demonstrated that pH 3.9 was more favorable than pH 3.65 or 3.4, leading to less degradation of vasopressin and greater stability. The good mass balance agreement between loss of assay and growth of the single co-eluting impurity peak for Impurity N, at higher temperatures and over time confirms that deamidation is the only observed degradation mechanism of the peptide. Finally, it was established that the vasopressin premix formulations provided herein with pH 3.65 or 3.9 can be stored at 25° C. for at least up to 12 months, and the vasopressin premix formulations provided herein with pH 3.9 can be stored at 25° C. for at least up to 24 months, since the vasopressin assay values remained within the 90-110% USP monograph limits for Vasopressin Injection after 12 months of 25° C. storage.

Example 4: Long Term Stability of Vasopressin Premix Formulations

The following example provides stability data for premix vasopressin formulations having concentrations of vasopressin ranging from 0.2 unit/mL (363 ng/mL) to 0.4 unit/mL (726 ng/ml) in water, with 3 mM (336 μg/mL) sodium D,L-lactate as buffer, and 0.9% (9 mg/mL) sodium chloride as an osmolality adjuster, and having a pH ranging from 3.6 to 4.0 (with sodium hydroxide and hydrochloric acid used as pH adjustors).

The following formulations were used in experiments in this example:

- vasopressin at 0.2 unit/mL, pH 3.6-4.0, 0.9% NaCl, 3 mM sodium D,L-lactate; and
- vasopressin at 0.4 unit/mL, pH 3.6-4.0, 0.9% NaCl, 3 mM sodium D,L-lactate. pH of each formulation was adjusted with sodium hydroxide and hydrochloric acid.

Vasopressin was stable and did not exhibit significant degradation in the formulations tested. Impurity data following testing of the above formulations indicated a slow increase at 25° C. and no change at 5° C. over shelf life storage for Related Compound N. No other Related Compound was observed above the reporting threshold during testing of the aforementioned formulations (the two tests are referred to as the developmental and registration stability studies) at either 5° C. or 25° C. storage.

Over time, and at an increasing rate with higher temperature, the vasopressin formulation provided herein slowly underwent deamidation at one of three available sites on the peptide to produce impurities. These three deamidation degradants are collectively referred to as Related Compound N and are described in FIG. 1.

Table 18 provides a summary of the stability studies. The data in Table 18 shows the highest mean impurity (Related Compound N) levels observed in the tested formulations (from the developmental and registration stability studies) in comparison to data from an alternative vasopressin formulation (referred to as "LD"). Test developmental formulations were exposed for 12 months at either 5° C. or 25° C. Registration stability test articles were exposed for 12 months at 5° C.±3° C. and 12 months at 25° C.±2° C./40%±5% RH. The LD was characterized after the maximum allowable 12 months of storage at 25° C., at expiry. The related compounds (% of vasopressin) in these formulations were measured at the indicated times using Method A described below As shown in Table 18, the percentages of Related Compound N and Total Related Compounds were comparable between the premix formulations provided herein and LD after 24 months at 5° C. The results demonstrate that the tested vasopressin premix formulations were stable for at least 24 months at 5° C., having stability that is at least comparable to LD, a concentrated vasopressin formulation that requires dilution prior to use.

Summaries of the batch analysis data for the 0.2 units/mL and 0.4 units/mL strengths of the vasopressin formulation of the present disclosure are provided in FIGS. 5 and 6, respectively.

Based upon the 12 months of long-term refrigerated (5° C.) and 12 months of accelerated (25° C.) stability data provided herein, the vasopressin premix formulations can be stably stored refrigerated at 36° F. to 46° F. (2° C. to 8° C.) for at least 12 months.

TABLE 18

Comparison of highest related impurity compound levels in tested vasopressin formulations

| Related Compound | Largest Mean Value Observed in Developmental Stability Units at 5° C. for 24 Months | Largest Mean Value Observed in Registration Stability Batches at 5° C. for 12 Months (% w/w) | Largest Mean Value Observed in LD at 5° C. for 24 Months (% w/w) | Largest Mean Value Observed in LD at 25° C. for up to 12 Months (% w/w) |
|---|---|---|---|---|
| Related Compound N | 0.8% | NMT 0.50% | 0.8% | 1.5% |
| Any Other Individual Related Compound | NMT 0.50% | NMT 0.50% | NMT 0.50% | NMT 0.50% |
| Total Related Compounds | 0.8% | NMT 0.50% | 0.8% | 1.5% |

NMT = Not More Than

Description of Method A and Method B

Where indicated, the below assays were used in the foregoing examples.

Vasopressin Assay and Impurity Analysis—Method A

The amount of vasopressin and impurities in formulations was measured using reverse phase high performance liquid chromatography (HPLC) using a C18 column (Millipore Sigma). Detection was performed using UV at 220 nm. The concentration of vasopressin was determined using an external standard. The following buffers were used:

Buffer A: 6.6 g/L ammonium phosphate, pH 3.0

Buffer B: 6.6 g/L ammonium phosphate, pH 3.0 mixed with acetonitrile 1:1 in volume Twenty (20) μL of each sample was injected into a YMC Triart C18 ExRS column 100×2.0 mm; 1.9 μm P/N TAR08SP9-1002 PT, with the column temperature at 40° C. Buffers A and B were run through the column at a flow rate of 0.6 mL per minute for 30 minutes with an increasing percentage of buffer B from time 0 (buffer B 15%) until 20 minutes (buffer B 50%), then buffer B 15% at 25 minutes until 30 minutes. The amount of vasopressin in the sample was determined by analyzing vasopressin peak in the sample relative to the vasopressin peak in standard samples that contained 1 U/mL or 0.1 U/mL vasopressin. Vasopressin degradation over time was determined based on the % of the initial (time=0) amount of vasopressin in each sample. Non-vasopressin peaks appeared over time relative to the blank injection. Total amounts of impurities were determined as the sum of all related compounds above the reporting threshold (0.1%) that were not attributed to the blank injection, and expressed as % of vasopressin ("% of main").

Vasopressin Assay and Impurity Analysis—Method B

The amount of vasopressin and impurities in formulations was measured by vasopressin assay and impurities analysis using HPLC as described in the Method A above with a few modifications (Method B). The differences between Method B from Method A are as follows:

Five hundred (500) μL sample was injected.

Standards include vasopressin at 0.1 U/mL.

What is claimed:

1. A method of increasing blood pressure in a human subject in need of increased blood pressure, the method comprising:

intravenously administering a therapeutically effective amount of a pharmaceutical premix vasopressin formulation to the human subject who is in need of increased blood pressure, wherein the pharmaceutical premix vasopressin formulation is not diluted prior to administration, wherein the pharmaceutical premix vasopressin formulation is in a primary container which is in a sealed container system for stable storage of the pharmaceutical premix vasopressin formulation, wherein the pharmaceutical premix vasopressin formulation is an aqueous formulation having a pH of about 3.1 to 4.5 and comprises about 0.1 unit/mL to about 1.0 unit/mL vasopressin or about 180 ng/ml to about 910 ng/mL vasopressin, sodium chloride, and sodium lactate, wherein the primary container is a multi-layer plastic container comprising a layer of polyethylene, wherein the primary container is an intravenous bag having a volume of 50 mL to 500 mL, and wherein the pharmaceutical premix vasopressin formulation is stable for at least 5 months at 25 degrees Celsius.

2. The method of claim 1, wherein the human subject has vasodilatory shock.

3. The method of claim 2, wherein the human subject remains hypotensive despite fluids and catecholamines.

4. The method of claim 1, comprising administering to the human subject the premix vasopressin formulation at a rate of about 0.03 to 0.1 units vasopressin per minute, wherein the subject has post-cardiotomy shock; or at a rate of about 0.01 to 0.07 units vasopressin per minute, wherein the subject has septic shock.

5. The method of claim 1, wherein the concentration of sodium chloride is about 8.5 mg/mL to about 9.5 mg/mL.

6. The method of claim 5, wherein the concentration of sodium chloride is about 9 mg/mL.

7. The method of claim 1, wherein the concentration of vasopressin is about 0.2 unit/mL to about 1 unit/mL vasopressin; about 0.1 unit/mL to about 0.5 unit/mL vasopressin; about 0.2 unit/mL to about 0.4 unit/mL vasopressin; or about 360 ng/mL to about 730 ng/ml vasopressin.

8. The method of claim 7, wherein the concentration of vasopressin is about 0.2 unit/mL, about 0.4 unit/mL, about 360 ng/mL, or about 730 ng/mL.

9. The method of claim 1, wherein the premix vasopressin formulation further comprises sodium hydroxide and/or hydrochloric acid as pH adjusters.

10. The method of claim 1, wherein the premix vasopressin formulation has a pH between about 3.6 and about 4.0.

11. The method of claim 1, wherein the concentration of the sodium lactate is about 2.5 mM to about 3.5 mM or about 280 μg/mL to about 400 μg/mL.

12. The method of claim 11, wherein the concentration of the sodium lactate is about 3 mM or about 336 μg/mL.

13. The method of claim 1, wherein the primary container has a volume of 50 mL to 250 mL.

14. The method of claim 1, wherein the primary container has a volume of about 100 mL and contains the premix vasopressin formulation of about 100 mL.

15. The method of claim 1, wherein the sodium lactate is sodium D,L-lactate.

16. The method of claim 1, wherein the primary container has a single port, the single port comprising an administration port for delivering the premix vasopressin formulation to the human subject.

17. A method of increasing blood pressure in a human subject in need of increased blood pressure, the method comprising intravenously administering a therapeutically effective amount of a pharmaceutical premix vasopressin formulation to the human subject who is in need of increased blood pressure, wherein the pharmaceutical premix vasopressin formulation is not diluted prior to administration, wherein the pharmaceutical premix vasopressin formulation is in a primary container which is in a sealed container system for stable storage of the pharmaceutical premix vasopressin, wherein the premix vasopressin formulation comprises about 0.1 unit/mL to about 1 unit/mL vasopressin, about 8.5 mg/mL to about 9.5 mg/mL sodium chloride, about 2.5 mM to about 3.5 mM or about 280 μg/mL to about 400 μg/mL sodium lactate, wherein the premix vasopressin formulation is an aqueous formulation and has a pH of about 3.1 to about 4.5, wherein the primary container is a multi-layer plastic container comprising a layer of polyethylene, wherein the primary container is an intravenous bag having a volume of 50 mL to 500 mL, and wherein the pharmaceutical premix vasopressin formulation is stable for at least 5 months at 25 degrees Celsius.

18. The method of claim 17, wherein the premix vasopressin formulation comprises about 0.2 unit/mL to about 1 unit/mL vasopressin; about 0.1 unit/mL to about 0.5 unit/mL vasopressin; about 0.2 unit/mL to about 0.4 unit/mL vasopressin; or about 360 ng/ml to about 730 ng/mL vasopressin.

19. The method of claim 17, wherein the premix vasopressin formulation comprises about 0.2 unit/mL, about 0.4 unit/mL, about 360 ng/ml, or about 730 ng/mL vasopressin.

20. The method of claim 17, wherein the human subject has vasodilatory shock.

21. The method of claim 20, wherein the human subject has vasodilatory shock and remains hypotensive despite fluids and catecholamines.

22. The method of claim 17, comprising administering to the human subject the premix vasopressin formulation at either a rate of about 0.03 to 0.1 units vasopressin per minute, wherein the subject has post-cardiotomy shock; or a rate of about 0.01 to 0.07 units vasopressin per minute, wherein the subject has septic shock.

23. A method of increasing blood pressure in a human subject in need of increased blood pressure, the method comprising intravenously administering a therapeutically effective amount of a pharmaceutical premix vasopressin formulation to the human subject who is in need of increased blood pressure, wherein the pharmaceutical premix vasopressin formulation is not diluted prior to administration, wherein the pharmaceutical premix vasopressin formulation is in a primary container which is in a sealed container system for stable storage of the pharmaceutical premix vasopressin formulation, wherein the pharmaceutical premix vasopressin formulation consists essentially of about 0.1 unit/mL to about 1 unit/mL vasopressin;

about 9 mg/mL sodium chloride, about 3 mM or about 336 μg/mL sodium lactate, and, optionally, a pH adjustor(s) which is sodium hydroxide and/or hydrochloric acid, wherein the pharmaceutical premix vasopressin formulation is an aqueous formulation and has a pH of about 3.5 to about 4.1, and wherein the primary container is an intravenous bag having a volume of 50 mL to 500 mL, and wherein the pharmaceutical premix vasopressin formulation is stable for at least 5 months at 25 degrees Celsius.

24. The method of claim 23, wherein the premix vasopressin formulation comprises about 0.2 unit/mL to about 1 unit/mL vasopressin; about 0.1 unit/mL to about 0.5 unit/mL vasopressin; about 0.2 unit/mL to about 0.4 unit/mL vasopressin; or about 360 ng/ml to about 730 ng/mL vasopressin.

25. The method of claim 23, wherein the premix vasopressin formulation comprises about 0.2 unit/mL, about 0.4 unit/mL, about 360 ng/mL, or about 730 ng/mL vasopressin.

26. The method of claim 23, wherein the human subject has vasodilatory shock.

27. The method of claim 26, wherein the human subject has vasodilatory shock and remains hypotensive despite fluids and catecholamines.

28. The method of claim 23, comprising administering to the human subject the premix vasopressin formulation at either a rate of about 0.03 to 0.1 units vasopressin per minute, wherein the subject has post-cardiotomy shock; or a rate of about 0.01 to 0.07 units vasopressin per minute, wherein the subject has septic shock.

* * * * *